(12) United States Patent
Moaddeb et al.

(10) Patent No.: US 8,449,604 B2
(45) Date of Patent: May 28, 2013

(54) ADJUSTABLE PROSTHETIC VALVE IMPLANT

(75) Inventors: Shawn Moaddeb, Irvine, CA (US); Samuel Shaolian, Newport Beach, CA (US); Emanuel Shaoulian, Newport Beach, CA (US); Jay A. Lenker, Laguna Beach, CA (US)

(73) Assignee: MiCardia Corporation, Irvine, CA (US)

( * ) Notice: Subject to any disclaimer, the term of this patent is extended or adjusted under 35 U.S.C. 154(b) by 0 days.

(21) Appl. No.: 12/544,163

(22) Filed: Aug. 19, 2009

(65) Prior Publication Data

US 2010/0185274 A1 Jul. 22, 2010

Related U.S. Application Data

(63) Continuation of application No. 11/638,473, filed on Dec. 14, 2006, now abandoned.

(60) Provisional application No. 60/751,036, filed on Dec. 16, 2005.

(51) Int. Cl.
*A61F 2/24* (2006.01)

(52) U.S. Cl.
USPC .......................... 623/2.1; 623/2.17; 623/2.18

(58) Field of Classification Search
USPC .............................. 623/2.14–2.19, 1.24, 1.26
IPC .......................................................... A61F 2/24
See application file for complete search history.

(56) References Cited

U.S. PATENT DOCUMENTS

| | | | |
|---|---|---|---|
| 4,503,569 A * | 3/1985 | Dotter | 623/1.19 |
| 5,217,484 A | 6/1993 | Marks | |
| 5,290,300 A | 3/1994 | Cosgrove | |
| 5,350,413 A | 9/1994 | Miller | |
| 5,354,295 A | 10/1994 | Guglielmi et al. | |
| 5,401,241 A | 3/1995 | Delany | |

(Continued)

OTHER PUBLICATIONS

Lutter, et al., *Percutaneous aortic valve replacement: an experimental study*, J of Thoracic & Card Surg, (2002).

(Continued)

*Primary Examiner* — Thomas J Sweet
*Assistant Examiner* — Jason-Dennis Stewart
(74) *Attorney, Agent, or Firm* — Knobbe, Martens, Olson & Bear, LLP

(57) ABSTRACT

A prosthetic implant for treating a diseased aortic valve is described. The prosthetic implant includes a substantially tubular body configured to be positioned in an aorta of a patient, at or near the patient's aortic valve. The body includes a lumen extending through the body from a proximal end to a distal end of the body; and an adjustable frame surrounding the lumen. The prosthetic implant further includes at least one adjustable element located in or on the body and extending at least partially around a circumference of the lumen. The at least one adjustable element includes a shape memory material and is transformable, in response to application of an activation energy, from a first configuration to a second configuration, wherein the first configuration and second configuration differ in a size of at least one dimension of the at least one adjustable element. The at least one adjustable element may engage at least one of a root of the aorta, an annulus of the aortic valve, and the patient's left ventricle, when the at least one adjustable element is in the second configuration.

28 Claims, 25 Drawing Sheets

U.S. PATENT DOCUMENTS

| | | | |
|---|---|---|---|
| 5,415,623 | A | 5/1995 | Cherubini |
| 5,476,471 | A | 12/1995 | Shifrin et al. |
| 5,509,888 | A | 4/1996 | Miller |
| 5,850,837 | A | 12/1998 | Shiroyama et al. |
| 5,882,302 | A | 3/1999 | Driscoll, Jr. et al. |
| 5,979,456 | A | 11/1999 | Magovern |
| 6,093,883 | A | 7/2000 | Sanghvi et al. |
| 6,160,084 | A | 12/2000 | Langer et al. |
| 6,167,313 | A | 12/2000 | Gray et al. |
| 6,168,615 | B1 | 1/2001 | Ken et al. |
| 6,273,908 | B1 | 8/2001 | Ndondo-Lay |
| 6,388,043 | B1 | 5/2002 | Langer et al. |
| 6,397,109 | B1 | 5/2002 | Cammilli et al. |
| 6,406,493 | B1 | 6/2002 | Tu et al. |
| 6,425,867 | B1 | 7/2002 | Vaezy et al. |
| 6,599,234 | B1 | 7/2003 | Gray et al. |
| 6,613,059 | B2 | 9/2003 | Schaller et al. |
| 6,638,293 | B1 | 10/2003 | Makower et al. |
| 6,718,985 | B2 | 4/2004 | Hlavka et al. |
| 6,720,402 | B2 | 4/2004 | Langer et al. |
| 6,730,118 | B2 | 5/2004 | Spenser et al. |
| 6,740,094 | B2 | 5/2004 | Maitland et al. |
| 6,786,904 | B2 | 9/2004 | Doscher et al. |
| 6,805,711 | B2 | 10/2004 | Quijano et al. |
| 6,849,088 | B2 | 2/2005 | Dehdashtian et al. |
| 6,893,160 | B2 | 5/2005 | Casey |
| 7,101,395 | B2 | 9/2006 | Tremulis et al. |
| 7,285,087 | B2 | 10/2007 | Moaddeb et al. |
| 7,297,150 | B2 | 11/2007 | Cartledge et al. |
| 2001/0021872 | A1 | 9/2001 | Bailey et al. |
| 2002/0138138 | A1 | 9/2002 | Yang |
| 2003/0153974 | A1 | 8/2003 | Spenser et al. |
| 2004/0210304 | A1 | 10/2004 | Seguin et al. |
| 2004/0236419 | A1 | 11/2004 | Milo |
| 2005/0075717 | A1 | 4/2005 | Nguyen et al. |

OTHER PUBLICATIONS

Younes, et al., *Steps toward percutaneous aortic valve replacement*, Circulation, J of Amer Heart Assoc, vol. 105, pp. 775-778 (2002).

Cribier, et al., *Early experience with percutaneous transcatheter implantation of heart valve prosthesis for the treatment of end-stage inoperable patients with calcific aortic stenosis*, J of Amer Coll of Card, vol. 43, pp. 698-703 (2004).

\* cited by examiner

ADJUSTABLE PROSTHETIC VALVE IMPLANT

CROSS-REFERENCE TO RELATED APPLICATIONS

This application is a continuation of U.S. patent application Ser. No. 11/638,473, filed Dec. 14, 2006 which claims the benefit under 35 U.S.C. §119(e) of U.S. Provisional Patent Application No. 60/751,036, filed on Dec. 16, 2005, and titled "ADJUSTABLE PROSTHETIC VALVE IMPLANT," the entireties of which are hereby incorporated by reference.

BACKGROUND OF THE INVENTION

1. Field of the Invention

The present invention relates to methods and devices for reinforcing dysfunctional heart valves and other body structures. More specifically, embodiments of the present invention relates to using an aortic valve prosthesis to treat a diseased aortic valve annulus.

2. Description of the Related Art

The circulatory system of mammals includes the heart and the interconnecting vessels throughout the body that include both veins and arteries. The human heart includes four chambers, which are the left and right atrium and the left and right ventricles. The mitral valve, which allows blood flow in one direction, is positioned between the left ventricle and left atrium. The tricuspid valve is positioned between the right ventricle and the right atrium. The aortic valve is positioned between the left ventricle and the aorta, and the pulmonary valve is positioned between the right ventricle and pulmonary artery. The heart valves function in concert to move blood throughout the circulatory system. The right ventricle pumps oxygen-poor blood from the body to the lungs and then into the left atrium. From the left atrium, the blood is pumped into the left ventricle and then out the aortic valve into the aorta. The blood is then recirculated throughout the tissues and organs of the body and returns once again to the right atrium.

If the valves of the heart do not function properly, due either to disease or congenital defects, the circulation of the blood may be compromised. Diseased heart valves may be stenotic, wherein the valve does not open sufficiently to allow adequate forward flow of blood through the valve, and/or incompetent, wherein the valve does not close completely. Incompetent heart valves cause regurgitation or excessive backward flow of blood through the valve when the valve is closed. For example, certain diseases of the heart valves can result in dilation of the heart and one or more heart valves. When a heart valve annulus dilates, the valve leaflet geometry deforms and causes ineffective closure of the valve leaflets. The ineffective closure of the valve can cause regurgitation of the blood, accumulation of blood in the heart, and other problems.

Aortic stenosis and aortic regurgitation are common diseases in an aging population. An effective therapy for these conditions is aortic valve replacement, in which damaged leaflets are excised and the diseased valve is sculpted to receive a replacement valve. Aortic valve replacement is usually accomplished by a surgical procedure, although endovascular procedures for valve replacement are an alternative. One endovascular procedure, percutaneous aortic valve replacement, is becoming a reality and brings new hope for a number of patients who cannot currently be treated with traditional surgical techniques.

Although surgical valve replacement concerns about 200,000 patients worldwide every year, it is estimated that up to two thirds of these patients do not receive surgery due to either excessive risk factors and comorbidities or patient refusal due to fear of lifestyle changes following heavy surgery in elderly patients. The size of this untreated population is expected to increase because of the aging population. Without replacing the valve, aortic stenosis is associated with a very high mortality rate (50 to 60% at one year) beyond the onset of symptoms. A percutaneous valve may bring a less invasive therapeutic solution for these patients.

Although a number of minimally invasive techniques for replacing heart valves do exist, they are often problematic. For example, with many minimally invasive valve replacements, paravalvular leaks can occur, with moderate to severe leakage occurring in 25% of cases. Paravalvular leakage may be due to sub-optimal implant size, shape, location, and the amount of morphology or calcification. These calcified lesions are extremely difficult to remove without fragmentation and without leaving some pieces of calcium, which may migrate and embolize. Accurate and secure deployment of the valve prostheses will remain a significant issue for these endovascular procedures.

The amount of reshaping or adjustment of the implants is important in these procedures. Excessive oversizing could cause reshaping of the valve annulus, but could reduce the likelihood of paravalvular leaks. The resultant paravalvular leak is somewhat unpredictable at the time of the implantation.

SUMMARY OF THE INVENTION

A need, therefore, remains for improved technology, which allows a device to be transluminally introduced, advanced into the region of the cardiac valve annulus, and implanted over the pathological natural valve. In certain embodiments, the device would be able to be guided by fluoroscopy, MRI or ultrasound. Certain embodiments would further allow for adjustment in size should perivalvular or paravalvular leakage be detected. Certain embodiments would further possess the capability for adjustment, both radially inward and radially outward, using non-surgical methodology.

In one embodiment, a prosthetic implant for treating a diseased aortic valve is disclosed. The prosthetic implant comprises a substantially tubular body configured to be positioned in an aorta of a patient, at or near the patient's aortic valve. The body comprises a lumen extending through the body from a proximal end to a distal end of the body; and an adjustable frame surrounding the lumen. The prosthetic implant further comprises at least one adjustable element located in or on the body and extending at least partially around a circumference of the lumen. The at least one adjustable element comprises a shape memory material and is transformable, in response to application of an activation energy, from a first configuration to a second configuration, wherein the first configuration and second configuration differ in a size of at least one dimension of the at least one adjustable element. The at least one adjustable element is configured to engage at least one of a root of the aorta, an annulus of the aortic valve, and the patient's left ventricle, when the at least one adjustable element is in the second configuration.

In certain embodiments, the at least one adjustable element is coupled to at least one prosthetic aortic valve leaflet. In certain embodiments, the at least one adjustable element comprises a prosthetic aortic valve annulus. In certain embodiments, the shape memory material is selected from the group consisting of shape memory metals, shape memory alloys, shape memory polymers, shape memory ferromagnetic alloys, and combinations thereof. In certain embodiments, the shape memory material comprises nitinol. In certain embodiments, the at least one dimension of the second configuration is greater than the at least one dimension of the first configuration. In certain embodiments, the at least one dimension of the second configuration is less than the at least one dimension of the first configuration. In certain embodiments, the at least one dimension is a diameter. In certain embodiments, the at least one dimension is a length. In certain embodiments, the at least one adjustable element is disposed in proximity to the open end of at least one of the distal end and the proximal end. In certain embodiments, a graft member covers at least a portion of at least one of the at least one adjustable element and the body. In certain embodiments, the implant further comprises at least a second adjustable element disposed between the distal end and the proximal end. In certain embodiments, the frame comprises the at least one adjustable element. In certain embodiments, the frame is expandable. In certain embodiments, the adjustable element comprises a closed ring. The closed ring may comprise a one-way ratchet. In certain embodiments, the adjustable element comprises an open ring. In certain embodiments, the adjustable element comprises a spiral portion. In certain embodiments, an insulating layer is disposed on at least a portion of the shape memory material. In certain embodiments, portions of the shape memory material are exposed through openings in the insulating layer. In certain embodiments, an energy-absorbing material is disposed on at least a portion of the shape memory material. In certain embodiments, the energy absorbing material absorbs ultrasonic energy. In certain embodiments, the energy absorbing material absorbs radio frequency energy. In certain embodiments, the adjustable element comprises wherein a wire loop that at least partially surrounds around a portion of the shape memory material. In certain embodiments, a check valve is affixed to a central region of the body. In certain embodiments, the check valve is a tri-leaflet check valve. In certain embodiments, the prosthetic implant further comprises an activation post configured to transmit activation energy to the at least one adjustable element. In certain embodiments, the prosthetic implant further comprises a crown support.

In one embodiment, a prosthetic implant for treating a diseased valve in a patient's aorta is disclosed. The prosthetic implant comprises valve means for permitting one-way flow of blood from the patient's left ventricle into the aorta. The prosthetic implant further comprises engagement means for engaging at least one of a root of the aorta, an annulus of the aortic valve, and the patient's left ventricle, the engagement means being coupled to the valve means. The prosthetic implant further comprises support means for supporting the valve means and coupled to the valve means, the support means being configured to extend distally into the ascending aorta beyond the aortic valve annulus when the valve means is in position at the aortic valve. The engagement means is adjustable from a first configuration to a second configuration in response to an activation energy established using an energy source external to the patient's body, wherein the first configuration and second configuration differ in size in at least one dimension. The engagement means engages the at least one of the root of the aorta, the annulus of the aortic valve, and the patient's left ventricle, when in the second configuration.

In one embodiment, a method, for treating an abdominal aortic aneurysm, is disclosed. The method comprises providing a prosthetic implant. The prosthetic implant comprises a substantially tubular body configured to be positioned in an aorta of a patient, at or near the patient's aortic valve. The body comprises a lumen extending through the body from a proximal end to a distal end of the body; and an adjustable frame surrounding the lumen. The prosthetic implant further comprises at least one adjustable element located in or on the body and extending at least partially around a circumference of the lumen. The at least one adjustable element comprises a shape memory material and is transformable, in response to application of an activation energy, from a first configuration to a second configuration, wherein the first configuration and second configuration differ in a size of at least one dimension of the at least one adjustable element. The at least one adjustable element is configured to engage at least one of a root of the aorta, an annulus of the aortic valve, and the patient's left ventricle, when the at least one adjustable element is in the second configuration. The method further comprises exposing the device to the activation energy, changing the at least one adjustable element from the first configuration to the second configuration.

In certain embodiments, the method further comprises implanting the prosthetic implant at the aortic valve region percutaneously. In certain embodiments, the implanting comprises expanding at least a portion of the prosthetic implant using a balloon. In certain embodiments, the device is exposed to the activation energy post-implantation. In certain embodiments, the device is exposed to an activation energy in multiple procedures. In certain embodiments, the method further comprises the activation energy comprises radio frequency energy. In certain embodiments, the activation energy comprises ultrasound energy. In certain embodiments, the activation energy comprises magnetic energy. In certain embodiments, the at least one adjustable element is imaged contemporaneously with exposure to the activation energy.

In one embodiment, a catheter device for activating an adjustable implant is disclosed. The catheter device comprises an elongate body having a proximal end and a distal end, the body configured to be placed within a patient's heart and/or aorta. The catheter device further comprises a first slot member, having a first slot, the first slot member disposed at the distal end of the body. The catheter device further comprises an energy-transfer member configured to couple to an activation post on a valve implant when the implant is located in the heart and the activation post is positioned at least partially within the slot member. The catheter device further comprises at least one activation lead configured to provide a transfer of energy between an energy source located outside of the patient and the energy-transfer member.

In certain embodiments, the energy-transfer member is configured to thermally couple to the activation post. In certain embodiments, the energy source is coupled to the proximal end of the catheter system. In certain embodiments, the first slot member further comprises a sharp edge configured to cut through tissue on the activation post. Certain embodiments of the adjustment catheter further comprise a second slot member, having a second slot, wherein the second slot is disposed at or near the distal end of the body. Certain embodiments of the adjustment catheter further comprise a locking member for securely coupling the activation post with the body. Certain embodiments of the adjustment catheter further comprise a spring-loaded tab within the slot or opening. Certain embodiments of the adjustment catheter further comprise radiopaque markers.

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE PREFERRED EMBODIMENT

Figure 1A:
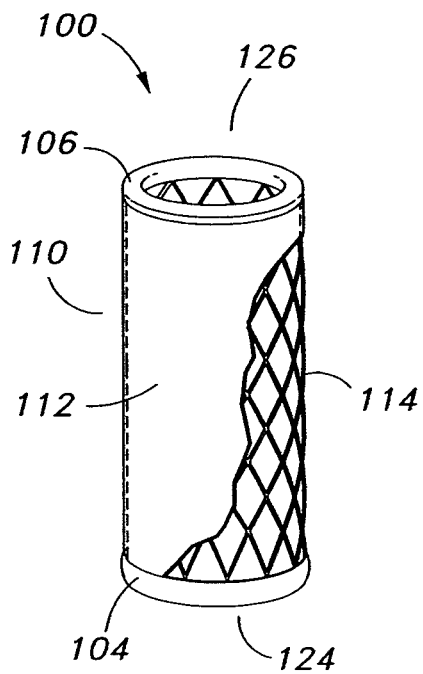
FIG. 1A illustrates an embodiment of an adjustable prosthetic valve implant that can be adjusted in vivo after implantation into a patient's body.

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

Embodiments of the present invention involve systems and methods for reinforcing dysfunctional heart valves and other body structures with adjustable implants. In certain embodiments, an adjustable prosthetic valve implant is implanted into the body of a patient such as a human or other animal. The adjustable prosthetic valve implant is implanted through an incision or body opening either thoracically (e.g., open-heart surgery) or percutaneously (e.g., via a femoral artery or vein, or other arteries or veins) as is known to someone skilled in the art. The adjustable prosthetic valve implant can be attached to the annulus of a heart valve, such as the aortic or mitral valve, to improve leaflet coaptation, to reduce regurgitation, and/or to reduce stenosis. The prosthetic valve implant may be selected from one or more shapes comprising a round or circular shape, an oval shape, a C-shape, a D-shape, a U-shape, an open circle shape, an open oval shape, and other curvilinear shapes.

The size of the prosthetic valve implant can be adjusted postoperatively to compensate for changes in the size of the heart. As used herein, the term "postoperatively" refers to a time after implanting the adjustable prosthetic valve implant and closing the body opening through which the adjustable prosthetic valve implant was introduced into the patient's body. For example, the prosthetic valve implant maybe implanted in a child whose heart grows as the child gets older. Thus, the size of the prosthetic valve implant may need to be increased. As another example, the size of an enlarged heart may start to return to its normal size after a prosthetic valve implant is implanted. Thus, the size of the prosthetic valve implant may need to be decreased postoperatively to continue to reinforce the heart valve annulus.

In certain embodiments, the prosthetic valve implant comprises a shape memory material that is responsive to changes in temperature and/or exposure to a magnetic field. Shape memory is the ability of a material to regain its shape after deformation. Shape memory materials include polymers, metals, metal alloys and ferromagnetic alloys. The prosthetic valve implant is adjusted in vivo by applying an energy source to activate the shape memory material and cause it to change to a memorized shape. The energy source may include, for example, thermal energy, radio frequency (RF) energy, x-ray energy, microwave energy, ultrasonic energy such as focused ultrasound, high intensity focused ultrasound (HIFU) energy, light energy, electric field energy, magnetic field energy, cryogenic energy, combinations of the foregoing, or the like. For example, one embodiment of electromagnetic radiation that is useful is infrared energy having a wavelength in a range between approximately 750 nanometers and approximately 1600 nanometers. This type of infrared radiation may be produced efficiently by a solid state diode laser. In certain embodiments, the prosthetic valve implant is selectively heated using short pulses of energy having an on and off period between each cycle. The energy pulses provide segmental heating which allows segmental adjustment of portions of the prosthetic valve implant without adjusting the entire implant. In some embodiments, the prosthetic valve implant has a first activation temperature for expanding its adjustable elements and a second activation temperature for contracting its adjustable elements.

In certain embodiments, the prosthetic valve implant includes an energy absorbing material to increase heating efficiency and localize heating in the area of the shape memory material. Thus, damage to the surrounding tissue is reduced or minimized. Energy absorbing materials for light or laser activation energy may include nanoshells, nanospheres and the like, particularly where infrared laser energy is used to energize the material. Such nanoparticles may be made from a dielectric, such as silica, coated with an ultra thin layer of a conductor, such as gold, and be selectively tuned to absorb a particular frequency of electromagnetic radiation. In certain such embodiments, the nanoparticles range in size between about 5 nanometers and about 20 nanometers and can be suspended in a suitable material or solution, such as saline solution. In certain embodiments, the nanoparticles range in size between about 2 nanometers and about 30 nanometers. In certain embodiments, the nanoparticles range in size between about 5 nanometers and about 20 nanometers. In certain embodiments, the nanoparticles range in size between about 8 nanometers and about 15 nanometers. Coatings comprising nanotubes or nanoparticles can also be used to absorb energy from, for example, HIFU, MRI, inductive heating, or the like.

In certain embodiments, thin film deposition or other coating techniques such as sputtering, reactive sputtering, metal ion implantation, physical vapor deposition, and chemical deposition can be used to cover portions or all of the prosthetic valve implant. Such coatings can be either solid or microporous. When HIFU energy is used, for example, a microporous structure traps and directs the HIFU energy toward the shape memory material. The coating improves thermal conduction and heat removal. In certain embodiments, the coating also enhances radio-opacity of the prosthetic valve implant. Coating materials can be selected from various groups of biocompatible organic or non-organic, metallic or non-metallic materials such as Titanium Nitride (TiN), Iridium Oxide (Irox), Carbon, Platinum black, Titanium Carbide (TiC), Graphite, Ceramic, and other materials used for pacemaker electrodes or implantable pacemaker leads. Other materials discussed herein or known in the art can also be used to absorb energy.

In certain embodiments, fine conductive wires such as platinum coated copper, titanium, tantalum, stainless steel, gold, or the like, are wrapped around the shape memory material to allow focused and rapid heating of the shape memory material while reducing undesired heating of surrounding tissues.

In certain embodiments, the energy source is applied surgically either during implantation or at a later time. For example, the shape memory material can be heated during implantation of the prosthetic valve implant by touching the prosthetic valve implant with warm object. As another example, the energy source can be surgically applied after the prosthetic valve implant has been implanted by percutaneously inserting a catheter into the patient's body and applying the energy through the catheter. For example, RF energy, light energy or thermal energy (e.g., from a heating element using resistance heating) can be transferred to the shape memory material through a catheter positioned on or near the shape memory material. Alternatively, thermal energy can be provided to the shape memory material by injecting a heated fluid through a catheter or circulating the heated fluid in a balloon through the catheter placed in close proximity to the shape memory material. As another example, the shape memory material can be coated with a photodynamic absorbing material which is activated to heat the shape memory material when illuminated by light from a laser diode or directed to the coating through fiber optic elements in a catheter. In certain such embodiments, the photodynamic absorbing material includes one or more drugs that are released when illuminated by the laser light.

In certain embodiments, the catheter may be guided to or coupled with the implant with the assistance of external means. In certain embodiments, the catheter can have additional sensors or electrodes to detect physiological or hemodynamic parameters. For example, the catheter may be capable of detecting pressure, temperature, ECG, and oxygen saturation. In certain embodiments, the catheter may comprise imaging capabilities. For example, a catheter capable of ultrasound imaging may have a built-in ultrasound transducer and may be linked with ultrasound imaging equipment. Such a catheter may allow simultaneous therapy and imaging.

In certain embodiments, a removable subcutaneous electrode or coil couples energy from a dedicated activation unit. In certain such embodiments, the removable subcutaneous electrode provides telemetry and power transmission between the system and the prosthetic valve implant. The subcutaneous removable electrode allows more efficient coupling of energy to the implant with minimum or reduced power loss. In certain embodiments, the subcutaneous energy is delivered via inductive coupling.

In certain embodiments, the energy source is applied in a non-invasive manner from outside the patient's body. In certain such embodiments, the external energy source is focused to provide directional heating to the shape memory material so as to reduce or minimize damage to the surrounding tissue. For example, in certain embodiments, a handheld or portable device comprising an electrically conductive coil generates an electromagnetic field that non-invasively penetrates the patient's body and induces a current in the prosthetic valve implant. The current heats the prosthetic valve implant and causes the shape memory material to transform to a memorized shape. In certain such embodiments, the prosthetic valve implant also comprises an electrically conductive coil wrapped around or embedded in the memory shape material. The externally generated electromagnetic field induces a current in the prosthetic valve implant's coil, causing it to heat and transfer thermal energy to the shape memory material. In certain embodiments, the prosthetic valve implant includes a coating, powder, slurry, paste, or combination of the foregoing, that absorbs energy from the electromagnetic field and transforms the energy into heat to change the temperature of the shape memory material. Such coatings may include, for example, a wide variety of magnetic and non-magnetic mixtures.

The term "magnetic" as used herein is a broad term and is used in its ordinary sense and includes, without limitation, any material that easily magnetizes, such as a material having atoms that orient their electron spins to conform to an external magnetic field. A magnetic coating may comprise materials exhibiting magnetic behavior or that may be magnetized by another magnet, including, but not limited to, ferromagnetism (including ferrimagnetism), diamagnetism and paramagnetism.

In certain embodiments, an external HIFU transducer focuses ultrasound energy onto the implanted prosthetic valve implant to heat the shape memory material. In certain such embodiments, the external HIFU transducer is a handheld or portable device. The terms "HIFU," "high intensity focused ultrasound" or "focused ultrasound" as used herein are broad terms and are used at least in their ordinary sense and include, without limitation, acoustic energy within a wide range of intensities and/or frequencies. For example, HIFU includes acoustic energy focused in a region, or focal zone, having an intensity and/or frequency that is considerably less than what is currently used for ablation in medical procedures. Thus, in certain such embodiments, the focused ultrasound is not destructive to the patient's cardiac tissue. In certain embodiments, HIFU includes acoustic energy within a frequency range of approximately 0.5 MHz and approximately 30 MHz and a power density within a range of approximately 1 $W/cm^2$ and approximately 500 $W/cm^2$.

In certain embodiments, the prosthetic valve implant comprises an ultrasound absorbing material or hydro-gel material that allows focused and rapid heating when exposed to the ultrasound energy and transfers thermal energy to the shape memory material. In certain embodiments, a HIFU probe is used with an adaptive lens to compensate for heart and respiration movement. The adaptive lens has multiple focal point adjustments. In certain embodiments, a HIFU probe with adaptive capabilities comprises a phased array or linear configuration. In certain embodiments, an external HIFU probe comprises a lens configured to be placed between a patient's ribs to improve acoustic window penetration and reduce or minimize issues and challenges regarding passing through bones. In certain embodiments, HIFU energy is synchronized with an ultrasound imaging device to allow visualization of the prosthetic valve implant during HIFU activation. In addition, in certain embodiments, ultrasound imaging is used to non-invasively monitor the temperature of tissue surrounding the prosthetic valve implant by using principles of speed of sound shift and changes to tissue thermal expansion.

In certain embodiments, non-invasive energy is applied to the implanted prosthetic valve implant using a Magnetic Resonance Imaging (MRI) device. In certain such embodiments, the shape memory material is activated by a constant magnetic field generated by the MRI device. In addition, in certain embodiments, the MRI device generates RF pulses that induce current in the prosthetic valve implant and heat the shape memory material. The prosthetic valve implant can include one or more coils and/or MRI energy absorbing material to increase the efficiency and directionality of the heating. Suitable energy absorbing materials for magnetic activation energy include particulates of ferromagnetic material. Suitable energy absorbing materials for RF energy include ferrite materials as well as other materials configured to absorb RF energy at resonant frequencies thereof, such as Fe—C, Fe—Pd, Fe—Mn—Si, Co—Mn, Fe—Co—Ni—Ti, Ni2MnGa, Co—Ni—Al, barium ferrite, barium boron, and the like.

In certain embodiments, the MRI device is used to determine the size of the implanted prosthetic valve implant before, during and/or after the shape memory material is activated. In certain such embodiments, the MRI device generates RF pulses at a first frequency to heat the shape memory material and at a second frequency to image the implanted prosthetic valve implant. Thus, the size of the prosthetic valve implant can be measured without heating the ring. In certain such embodiments, an MRI energy absorbing material heats sufficiently to activate the shape memory material when exposed to the first frequency and does not substantially heat when exposed to the second frequency. Other imaging techniques known in the art can also be used to determine the size of the implanted ring including, for example, ultrasound imaging, computed tomography (CT) scanning, X-ray imaging, or the like. In certain embodiments, such imaging techniques also provide sufficient energy to activate the shape memory material.

In certain embodiments, imaging and resizing of the prosthetic valve implant is performed as a separate procedure at some point after the prosthetic valve implant has been surgically implanted into the patient's heart and the patient's heart, pericardium and chest have been surgically closed. However, in certain embodiments, it is advantageous to perform the imaging after the heart and/or pericardium have been closed, but before closing the patient's chest, to check for leakage or the amount of regurgitation. If the amount of regurgitation remains excessive after the prosthetic valve implant has been implanted, energy from the imaging device (or from another source as discussed herein) can be applied to the shape memory material so as to at least partially contract the prosthetic valve implant and reduce regurgitation to an acceptable level. Thus, the success of the surgery can be checked and corrections can be made, if necessary, before closing the patient's chest.

In certain embodiments, activation of the shape memory material is synchronized with the heart beat during an imaging procedure. For example, an imaging technique can be used to focus HIFU energy onto a prosthetic valve implant in a patient's body during a portion of the cardiac cycle. As the heart beats, the prosthetic valve implant may move in and out of this area of focused energy. To reduce damage to the surrounding tissue, the patient's body is exposed to the HIFU energy during portions of the cardiac cycle that focus the HIFU energy onto the cardiac ring. In certain embodiments, the energy is gated with a signal that represents the cardiac cycle such as an electrocardiogram signal. In certain such embodiments, the synchronization and gating is configured to allow delivery of energy to the shape memory materials at specific times during the cardiac cycle to avoid or reduce the likelihood of causing arrhythmia or fibrillation during vulnerable periods. For example, the energy can be gated so as to expose the patient's heart to the energy during the T wave of the electrocardiogram signal.

As discussed above, shape memory materials include, for example, polymers, metals, and metal alloys including ferromagnetic alloys. Exemplary shape memory polymers that are usable for certain embodiments of the present invention are disclosed by Langer, et al. in U.S. Pat. No. 6,720,402, issued Apr. 13, 2004, U.S. Pat. No. 6,388,043, issued May 14, 2002, and U.S. Pat. No. 6,160,084, issued Dec. 12, 2000, each of which are hereby incorporated by reference herein. Shape memory polymers respond to changes in temperature by changing to one or more permanent or memorized shapes. In certain embodiments, the shape memory polymer is heated to a temperature between approximately 38 degrees Celsius and approximately 60 degrees Celsius. In certain embodiments, the shape memory polymer is heated to a temperature in a range between approximately 40 degrees Celsius and approximately 55 degrees Celsius. In certain embodiments, the shape memory polymer has a two-way shape memory effect wherein the shape memory polymer is heated to change it to a first memorized shape and cooled to change it to a second memorized shape. The shape memory polymer can be cooled, for example, by inserting or circulating a cooled fluid through a catheter.

Shape memory polymers implanted in a patient's body can be heated non-invasively using, for example, external light energy sources such as infrared, near-infrared, ultraviolet, microwave and/or visible light sources. The light energy may be selected to increase absorption by the shape memory polymer and reduce absorption by the surrounding tissue. Thus, damage to the tissue surrounding the shape memory polymer is reduced when the shape memory polymer is heated to change its shape. In certain embodiments, the shape memory polymer comprises gas bubbles or bubble containing liquids such as fluorocarbons and is heated by inducing a cavitation effect in the gas/liquid when exposed to HIFU energy. In certain embodiments, the shape memory polymer may be heated using electromagnetic fields and may be coated with a material that absorbs electromagnetic fields.

Certain metal alloys have shape memory qualities and respond to changes in temperature and/or exposure to magnetic fields. Exemplary shape memory alloys that respond to changes in temperature include titanium-nickel, copper-zinc-aluminum, copper-aluminum-nickel, iron-manganese-silicon, iron-nickel-aluminum, gold-cadmium, combinations of the foregoing, and the like. In certain embodiments, the shape memory alloy comprises a biocompatible material such as a titanium-nickel alloy. Shape memory alloys may comprise binary allow compositions, ternary allow compositions, or any of their combinations.

Shape memory alloys exist in two distinct solid phases called martensite and austenite. The martensite phase is relatively soft and easily deformed, whereas the austenite phase is relatively stronger and less easily deformed. For example, shape memory alloys enter the austenite phase at a relatively high temperature and the martensite phase at a relatively low temperature. Shape memory alloys begin transforming to the martensite phase at a start temperature ($M_s$) and finish transforming to the martensite phase at a finish temperature ($M_f$). Similarly, such shape memory alloys begin transforming to the austenite phase at a start temperature ($A_s$) and finish transforming to the austenite phase at a finish temperature ($A_f$). Both transformations have a hysteresis. Thus, the $M_s$ temperature and the $A_f$ temperature are not coincident with each other, and the $M_f$ temperature and the $A_s$ temperature are not coincident with each other.

In certain embodiments, the shape memory alloy is processed to form a memorized shape in the austenite phase in the form of a ring or partial ring. The shape memory alloy is then cooled below the $M_f$ temperature to enter the martensite phase and deformed into a larger or smaller ring. For example, in certain embodiments, the shape memory alloy is formed into a ring or partial ring that is larger than the memorized shape but still small enough to improve leaflet coaptation and reduce regurgitation in a heart valve upon being attached to the heart valve annulus. In certain such embodiments, the shape memory alloy is sufficiently malleable in the martensite phase to allow a user such as a physician to adjust the circumference of the ring in the martensite phase by hand to achieve a desired fit for a particular heart valve annulus. After the ring is attached to the heart valve annulus, the circumference of the ring can be adjusted non-invasively by heating the shape memory alloy to an activation temperature (e.g., temperatures ranging from the $A_s$ temperature to the $A_f$ temperature).

Thereafter, when the shape memory alloy is exposed to a temperature elevation and transformed to the austenite phase, the alloy changes in shape from the deformed shape to the memorized shape. Activation temperatures at which the shape memory alloy causes the shape of the prosthetic valve implant to change shape can be selected and built into the prosthetic valve implant such that collateral damage is reduced or eliminated in tissue adjacent the prosthetic valve implant during the activation process. Exemplary $A_f$ temperatures for suitable shape memory alloys range between approximately 45 degrees Celsius and approximately 70 degrees Celsius. Furthermore, exemplary $M_S$ temperatures range between approximately 10 degrees Celsius and approximately 20 degrees Celsius, and exemplary $M_f$ temperatures range between approximately −1 degrees Celsius and approximately 15 degrees Celsius. The size of the prosthetic valve implant can be changed all at once or incrementally in small steps at different times in order to achieve the adjustment necessary to produce the desired clinical result.

Certain shape memory alloys may further include a rhombohedral phase, having a rhombohedral start temperature ($R_s$) and a rhombohedral finish temperature ($R_f$), that exists between the austenite and martensite phases. An example of such a shape memory alloy is a NiTi alloy, which is commercially available from Memry Corporation (Bethel, Conn.). In certain embodiments, an exemplary $R_s$ temperature range is between approximately 30 degrees Celsius and approximately 50 degrees Celsius, and an exemplary $R_f$ temperature range is between approximately 20 degrees Celsius and approximately 35 degrees Celsius. One benefit of using a shape memory material having a rhombohedral phase is that in the rhombohedral phase the shape memory material may experience a partial physical distortion, as compared to the generally rigid structure of the austenite phase and the generally deformable structure of the martensite phase.

Certain shape memory alloys exhibit a ferromagnetic shape memory effect wherein the shape memory alloy transforms from the martensite phase to the austenite phase when exposed to an external magnetic field. The term "ferromagnetic" as used herein is a broad term and is used in its ordinary sense and includes, without limitation, any material that easily magnetizes, such as a material having atoms that orient their electron spins to conform to an external magnetic field. Ferromagnetic materials include permanent magnets, which can be magnetized through a variety of modes, and materials, such as metals, that are attracted to permanent magnets. Ferromagnetic materials also include ceramic magnets, which are electrically non-conductive ferrimagnetic ceramic compound materials comprising various mixtures of iron oxides such as Hematite or Magnetite and the oxides of other metals. Ferromagnetic materials also include electromagnetic materials that are capable of being activated by an electromagnetic transmitter, such as one located outside the heart 100. Furthermore, ferromagnetic materials may include one or more polymer-bonded magnets, wherein magnetic particles are bound within a polymer matrix, such as a biocompatible polymer. The magnetic materials can comprise isotropic and/or anisotropic materials, such as for example NdFeB (Neodynium Iron Boron), SmCo (Samarium Cobalt), ferrite and/or AlNiCo (Aluminum Nickel Cobalt) particles.

Thus, a prosthetic valve implant comprising a ferromagnetic shape memory alloy can be implanted in a first configuration having a first shape and later changed to a second configuration having a second (e.g., memorized) shape without heating the shape memory material above the $A_s$ temperature. Advantageously, nearby healthy tissue is not exposed to high temperatures that could damage the tissue. Further, since the ferromagnetic shape memory alloy does not need to be heated, the size of the prosthetic valve implant can be adjusted more quickly and more uniformly than by heat activation.

Exemplary ferromagnetic shape memory alloys include Fe—C, Fe—Pd, Fe—Mn—Si, Co—Mn, Fe—Co—Ni—Ti, Ni—Mn—Ga, $Ni_2MnGa$, Co—Ni—Al, and the like. Certain of these shape memory materials may also change shape in response to changes in temperature. Thus, the shape of such materials can be adjusted by exposure to a magnetic field, by changing the temperature of the material, or both.

In certain embodiments, combinations of different shape memory materials are used. For example, prosthetic valve implants according to certain embodiments comprise a combination of shape memory polymer and shape memory alloy (e.g., NiTi). In certain such embodiments, a prosthetic valve implant comprises a shape memory polymer tube and a shape memory alloy (e.g., NiTi) disposed within the tube. Such embodiments are flexible and allow the size and shape of the shape memory to be further reduced without impacting fatigue properties. In addition, in certain embodiments, shape memory polymers are used with shape memory alloys to create a bi-directional (e.g., capable of expanding and contracting) prosthetic valve implant. Bi-directional prosthetic valve implants can be created with a wide variety of shape memory material combinations having different characteristics.

In the following description, reference is made to the accompanying drawings, which form a part hereof, and which show, by way of illustration, specific embodiments or processes in which the invention may be practiced. Where possible, the same reference numbers are used throughout the drawings to refer to the same or like components. In some instances, numerous specific details are set forth in order to provide a thorough understanding of the present disclosure. The present disclosure, however, may be practiced without the specific details or with certain alternative equivalent components and methods to those described herein. In other instances, well-known components and methods have not been described in detail so as not to unnecessarily obscure aspects of the present disclosure.

FIG. 1A illustrates an adjustable prosthetic valve implant 100 according to certain embodiments that can be adjusted in vivo after implantation into a patient's body. The prosthetic valve implant 100 comprises an axially elongate hollow tubular body member 110 having a proximal end 126 and a distal end 124. As defined herein, a location that is defined as proximal is closer to the user than a location that is defined as distal. The illustrated embodiment further comprises a deformable or adjustable ring 106 at its proximal end 126 and a deformable or adjustable ring 104 at its distal end 124. In certain embodiments, the prosthetic valve implant 100 comprises an artificial valve.

The diameters of a catheter or implant are often measured in "French Size" which can be defined as three times the diameter in millimeters (mm). For example, a 15 French catheter is five millimeters in diameter. The French size is designed to approximate the circumference of the catheter in millimeters and is often useful for catheters that have non-circular cross-sectional configurations. Although the original measurement of "French" used π (3.14159 . . . ) as the conversion factor between diameters in millimeters and French, the system today uses a conversion factor of three.

In the illustrated embodiment, the prosthetic valve implant 100 is substantially symmetrical, that is, the prosthetic valve implant 100 is substantially similar in outer diameter or transverse dimension from the distal end of the tubular member 124 to the proximal end 126. As used herein, "dimension" is a broad term having its ordinary and customary meaning and includes a size or distance from a first point to a second point along a line or arc. For example, a dimension may be a circumference, diameter, radius, arc length, or the like. As another example, a dimension may be a distance between an anterior portion and a posterior portion of an annulus. In certain embodiments, the size of the dimension of an adjustable element or an annulus may be an intertrigonal length, anteroposterior length, a side-side (lateral) length, oblique or diagonal length, or other length. In certain embodiments, the prosthetic valve implant 100 is not symmetrical.

The prosthetic valve implant 100 has a longitudinal axis and has one or more internal lumens that extend from the proximal end 126 to the distal end 124 for the passage of instruments, fluids, tissue, or other materials. The axially elongate hollow tubular structure is generally flexible and capable of bending, to a greater or lesser degree, through one or more arcs in one or more directions perpendicular to the main longitudinal axis, so as to facilitate delivery of the implant.

In certain embodiments, the tubular structure 110 comprises a graft member 112 and a frame 114. The graft member 112 defines a lumen through which blood is directed, thereby providing an unimpeded flow of blood, such as from the heart into the aorta. The diameters of the lumens under physiological conditions will vary depending on sizes of the heart and aorta of the patient. The frame 114 provides mechanical support to the prosthetic valve implant 100, and in some embodiments, anchors the implant 100 to at least some degree. FIG.

1 shows part of the graft member 112 cut away in order to illustrate the frame 114 of which the implant 100 is comprised.

In certain embodiments, the implant 100 comprises an artificial heart valve (not illustrated). In certain embodiments, the artificial heart valve may be a mechanical valve. In certain embodiments, the artificial heart valve may be a biological (tissue) valve, such as a porcine valve. In certain embodiments, the artificial heart valve may be a check valve. In certain embodiments, the artificial heart valve may be another type of artificial valve. In certain embodiments the artificial heart valve may be located in a central section of the implant 100. In certain embodiments, the artificial valve may be located in another section of the implant.

In some embodiments, the graft member 112 comprises a graft fabric that is substantially impermeable to body fluids, for example, blood and/or plasma. The graft fabric comprises one or more biocompatible materials known in the art, for example, polyester (Dacron®), polyamide (Nylon@, Delrin®), polyimide (PI), polyetherimide (PEI), polyetherketone (PEEK), polyamide-imide (PAI), polyphenylene sulfide (PPS), polysulfone (PSU), silicone, woven velour, polyurethane, polytetrafluoroethylene (PTFE, Teflon®), expanded PTFE (ePTFE), fluoroethylene propylene (FEP), perfluoralkoxy (PFA), ethylene-tetrafluoroethylene-copolymer (ETFE, Tefzel®), ethylene-chlorotrifluoroethylene (Halar®), polychlorotrifluoroethylene (PCTFE), polychlorotrifluoroethylene (PCTE, Aclar®, Clarus®), polyvinyfluoride (PVF), polyvinylidenefluoride (PVDF, Kynar®, Solef®), fluorinated polymers, polyethylene (PE, Spectra®), polypropylene (PP), ethylene propylene (EP), ethylene vinylacetate (EVA), polyalkenes, polyacrylates, polyvinylchloride (PVC), polyvinylidenechloride, polyether block amides (PEBAX), polyaramid (Kevlar®), heparin-coated fabric, or the like. In some embodiments, the graft member 112 comprises reinforcing fibers known in the art, for example, fibers made from the materials discussed above, as well as fibers made from metal, steel, stainless steel, NiTi, metal alloys, carbon, boron, ceramic, polymer, glass, polymers, biopolymers, silk protein, cellulose, collagen, combinations thereof, and the like. In certain embodiments, the graft member 112 comprises a biological material, for example, a homograft, a patient graft, or a cell-seeded tissue. Combinations and/or composites are also suitable.

In some embodiments, the graft fabric comprises a laminate and/or composite having two or more layers. In some embodiments, the graft member 112 comprises a laminated graft fabric. In some embodiments, the laminate comprises one or more biologically active layers, for example, an inner and/or outer layer conducive to the proliferation of endothelial tissue, and/or that releases a drug, therapeutic agent, anti-coagulant, anti-proliferant, anti-inflammatory agent, and/or tissue growth modulating agent. In some embodiments, the laminate comprises one or more mechanical and/or reinforcing layers, comprising, for example, mesh and/or fabric layers, and/or reinforcing fibers. The fabric layers are woven or non-woven. Methods for manufacturing laminated/composite fabrics are known in the art, for example, using adhesives, thermal bonding, in situ curing, and the like. Those skilled in the art will understand that such layers for useful for providing the graft member 112 with desired mechanical properties, for example, strength, elasticity, and/or the like. For example, in some embodiments, the graft fabric is elastomeric, thereby permitting the graft member 112 to expand and contract in response to blood pressure changes. In some embodiments, the graft member 112 in its maximally expanded state under physiological conditions is smaller than the aorta. In some embodiments, the graft member 112 in its maximally expanded state under physiological conditions is larger than the aorta. In some embodiments, the mechanical properties of the graft member 112 are anisotropic. For example, in some embodiments, the graft member 112 is more expandable circumferentially than longitudinally.

In some embodiments, the graft member 112 has a substantially uniform thickness. In certain embodiments, the graft member 112 comprises areas of different thicknesses. For example, some embodiments of a fabric laminate graft member 112 comprise extra reinforcement in areas subject to stress, for example, where the graft member 112 is likely to contact the frame 114, and/or around the ends 124 and 126 of the tubular member 110. In some embodiments, the graft fabric is from about 0.25 mm to about 2.5 mm thick. In some embodiments, the graft fabric is from about 0.15 mm to about 4.0 mm thick. In some embodiments, the graft fabric is from about 0.05 mm to about 5.0 mm thick.

The frame 114 is of any suitable type known in the art. In some embodiments, the frame 114 comprises a metal, for example, titanium, steel, stainless steel, and/or, nitinol. In some embodiments, the frame 114 comprises a non-metal, for example, a polymer or ceramic. The polymer is rigid, flexible, and/or elastomeric. In some embodiments, the frame 114 comprises a composite. In some embodiments, the frame 114 is substantially unitary. In some embodiments, the frame 114 comprises a plurality of components or subassemblies. In some embodiments, the frame 114 comprises one or more structures and/or subcomponents fabricated from wire. The term "wire" is a broad term having its normal and customary meaning and includes, for example, mesh, flat, round, rod-shaped, or band-shaped members, as well as solid, hollow or tubular elongated structures that may in cross-section be cylindrical, elliptical, polygonal, or any other shape, including a substantially flat ribbon shape. In certain embodiments, the frame 114 comprises shape memory materials, as described above.

In some embodiments, the frame 114 comprises one or more structures and/or subcomponents fabricated from a sheet and/or billet, for example, by stamping, drilling, cutting, forging, shearing, machining, etching, and the like. In some embodiments, the frame 114 is at least partially self-deploying. In some embodiments, a deployment device is used, for example, a balloon. In certain embodiments, the frame 114 comprises securing means for securing the implant 100, for example, hooks, barbs, spikes, protrusions, and the like. The securing means are disposed on the frame 114 at or around the exterior of the proximal end 126 and distal end 124. In some embodiments, the frame 114 comprises one or more biologically active compounds and/or active chemical entities known in the art, for example, a drug, therapeutic agent, anti-coagulant, anti-proliferant, anti-inflammatory agent, and/or tissue growth modulating agent. In the illustrated embodiment, the frame 114 comprises a stent.

The illustrated embodiment 100 comprises a plurality of adjustable elements which, in the illustrated embodiment, are adjustable rings 104 and 106. Those skilled in the art will understand that the following description of the adjustable rings 104 and 106 is equally applicable to other types of adjustable elements. As used, the term "ring" broadly refers to shapes that are closed or open. In the illustrated embodiment, the adjustable rings 104 and 106 are substantially circular, closed rings.

In certain embodiments, the prosthetic valve implant may comprise additional adjustable rings. For example, in certain embodiments, the prosthetic valve implant may comprise an adjustable ring in a location substantially equidistant from the rings 106 and 104 located at the proximal and distal ends 126 and 124 of the implant 100, respectively.

In the illustrated embodiment, adjustable rings 106 and 104 are located at the proximal 126 and distal ends 124 of the implant 100, respectively. In some embodiments, one or more of the adjustable rings are secured to the frame 114, to the graft member 112, or to the frame 114 and the graft member 112. Each of the adjustable rings 104 and 106 is independently selected from one or more shapes, for example, a round or circular shape, an oval shape, a C-shape, a D-shape, a U-shape, an open circle shape, an open oval shape, other curvilinear shapes, spiral shapes, and other suitable shapes.

Each of the adjustable rings 104 and 106 independently have any suitable cross-sectional shape. In some embodiments, the adjustable rings 104 and 106 have substantially, circular, elliptical, ovoid, rectangular, trapezoidal, square, triangular, and/or hexagonal cross sections. In some embodiments, an adjustable ring may comprise an adjustable wire. Those skilled in the art will understand that in some embodiments, the cross sectional shape assists in the securing of one or more of the adjustable rings 104 and 106 to the body 110, as discussed above. In some embodiments, one or more of the adjustable rings 104 and 106 comprises means for securing the implant 100 in the body, for example, hooks, barbs, spikes, protrusions, and the like.

The outer diameter of the adjustable rings 104 and 106 is expandable and/or contractible. In some embodiments, another dimension of the adjustable rings 104 and 106 is also adjustable, for example, the length. In some embodiments, the dimensional change(s) are substantially isotropic, while in some embodiments, the changes are anisotropic. For example, in some embodiments, a substantially circular adjustable ring is substantially elliptical after adjustment.

The adjustable rings 104 and 106 independently comprise one or more of the shape memory materials discussed herein, for example, metals, alloys, polymers, and/or ferromagnetic alloys. In some embodiments, one or more of the adjustable rings 104 and 106 comprises a shape memory material that responds to the application of temperature that differs from a nominal ambient temperature, for example, the nominal body temperature of 37 degrees Celsius for humans. In some embodiments, the shape memory material is nitinol. Heating the adjustable ring above the austenite temperature of the shape memory material induces the adjustable ring to return to the memorized shape.

In some embodiments, the adjustable rings 104 and 106 are expandable. In some embodiments, each of the adjustable rings 104 and 106 has on outer diameter of from about 0.5 cm to about 1.5 cm in an unadjusted configuration. In some embodiments, each of the adjustable rings 104 and 106 has on outer diameter of from about 1 cm to about 2 cm in an adjusted configuration. In some embodiments, the expansion percentages for the adjustable rings 104 and 106 is from about 6% to about 23%, where the expansion percentage is the difference between the starting and finishing diameter of the adjustable ring divided by the starting diameter. In some embodiments, the expansion percentages for the adjustable rings 104 and 106 is from about 3% to about 35%. Those skilled in the art will understand that different sized adjustable rings 104 and 106 are useful for different patients, such as adjustable rings with sizes smaller than 0.25 cm or larger than 1.5 cm.

The activation temperatures (e.g., temperatures ranging from the $A_s$ temperature to the $A_f$ temperature) at which an adjustable element expands to an increased circumference are selected and built into an adjustable element such that collateral damage is reduced or eliminated in tissue adjacent the adjustable element during the activation process. In certain embodiments, the activation temperatures for shape memory material of an adjustable element at which substantially maximum expansion occurs are in a range between about 38 degrees Celsius and about 1310 degrees Celsius. In some embodiments, the activation temperatures are in a range between about 39 degrees Celsius and about 75 degrees Celsius. For some embodiments that include shape memory polymers for an adjustable element, activation temperatures at which the glass transition of the material or substantially maximum contraction occur range between about 38 degrees Celsius and about 60 degrees Celsius. In some embodiments, the activation temperature is in a range between about 40 degrees Celsius and about 59 degrees Celsius.

In some embodiments, the austenite start temperature $A_s$ is in a range between about 33 degrees Celsius and about 43 degrees Celsius, the austenite finish temperature $A_f$ is in a range between about 45 degrees Celsius and about 55 degrees Celsius, the martensite start temperature $M_s$, is less than about 30 degrees Celsius, and the martensite finish temperature $M_f$ is greater than about 20 degrees Celsius. In some embodiments, the austenite finish temperature $A_f$ is in a range between about 48.75 degrees Celsius and about 51.25 degrees Celsius. Certain embodiments can include other start and finish temperatures for martensite, rhombohedral and austenite phases as described herein.

In some embodiments, an adjustable element is shape set in the austenite phase to a remembered configuration during its manufacturing such that the remembered configuration has a relatively larger diameter. After cooling the adjustable element below the $M_f$ temperature, it is mechanically deformed to a relatively smaller diameter to achieve a desired starting nominal diameter. In some embodiments, the adjustable element is sufficiently malleable in the martensite phase to allow a user, such as a physician, to manually adjust the circumferential value to achieve a desired fit the for the appropriate heart valve.

In some embodiments, one or more of the adjustable rings 104 and 106 comprises a plurality of components. For example, in some embodiments, an adjustable ring 104 and 106 comprises a body and a means for securing the ring to the body 110, for example, screws, pins, a lock ring, a snap ring, latches, detents, springs, clips, combinations thereof, and the like. In some embodiments, one or more of the adjustable rings 104 and 106 comprise a plurality of shape memory materials, each of which is adjustable under different conditions. For example, in some embodiments, an adjustable element comprises a plurality of shape memory materials with different $A_f$ temperatures, thereby permitting a stepwise and/or sequential adjustment of the adjustable element using selective heating and/or cooling, as discussed below. In some embodiments, an adjustable element comprises two or more shape memory materials that adjust by different mechanisms, for example, a thermal shape memory material and a ferromagnetic shape memory material.

In the illustrated embodiment, the adjustable rings 104 and 106 are secured to both the graft member 112 and the frame 114 by means known in the art, for example, by suturing, adhesively, mechanically, manufacturing integrally into the body 110, thermal welding and/or bonding, or combinations thereof. Examples of suitable adhesives are known in the art, and include polyurethane, polyurea, epoxide, synthetic rubbers, silicone, and mixtures, blends, and copolymers thereof. The adhesive(s) may be UV curing, thermally curing, thermoplastic, and/or thermosetting. Suitable mechanical securing means include lock rings, snap rings, pins, screws, latches, detents, springs, clips, swaging, heat shrinking, and the like. Thermal welding or bonding is performed with or without an intermediate bonding layer, for example, a thermoplastic bonding film (e.g., polyethylene, polychlorotrifluoroethylene, and/or fluoroethylene propylene). In some embodiments, at least one of the adjustable rings 104 and 106 is integral with at least a portion of the frame 114, for example, formed in the same manufacturing step. In some embodiments, at least one of the adjustable rings 104 and 106 is secured to at least a portion of the frame 114 as discussed above.

In some embodiments, at least one of the adjustable rings 104 and 106 comprises a porous structure and/or a fabric, which provides a point of attachment for the graft material and/or frame material. In some embodiments, the porous structure is useful for drug delivery, as discussed below. In some embodiments, the at least a portion of one of the adjustable rings 104 and 106 comprises one or more biologically active compounds and/or active chemical entities known in the art, for example, a drug, therapeutic agent, anti-coagulant, anti-proliferant, anti-inflammatory agent, and/or tissue growth modulating agent. In some embodiments, at least a portion of one of the adjustable rings 104 and 106 is covered and/or coated with a biodegradable/biocompatible material known in the art, for example, polylactic acid (PLA). In some embodiments, this coating facilitates removal.

In the illustrated embodiment, the graft member 112 is secured to adjustable rings 104 and 106 as discussed above. In some embodiments, the graft member 112 also secured to the frame 114 by means known in the art, for example, using sutures, adhesives, mechanically, thermal welding and/or bonding, or combinations thereof. These methods are described in greater detail above. In some embodiments, the graft member 112 is secured to the frame 114 at or near the end of the proximal end 126 or the distal end 124 of the implant 100. In some embodiments, the graft member 112 is secured to the frame 114 at another location. In some embodiments, securing the graft member 112 to the frame 114 provides one or more advantages, for example, improved durability or strength, and/or increased lumen size, which provides improved blood flow.

The prosthetic valve implant 100 is sized to facilitate implantation, such as percutaneous implantation through the femoral artery. In some embodiments, the graft implant 100 is loaded in an introduction or deployment catheter in a collapsed configuration (not illustrated), the catheter inserted into the femoral artery percutaneously, the catheter advanced to the left ventricle, the prosthetic valve implant 100 deployed from the catheter, the prosthetic valve implant 100 implanted, for example, using a balloon, and the introduction catheter and balloon removed. In some embodiments, the diameters of one or more of the adjustable rings 104 and/or 106 are adjusted during implantation, for example, using a balloon and/or other means known in the art.

In some embodiments, the valve implant 100 is adjusted in vivo by applying an energy source, for example, radio frequency energy, X-ray energy, microwave energy, ultrasonic energy such as high intensity focused ultrasound (HIFU) energy, light energy, electric field energy, magnetic field energy, combinations of the foregoing, or the like. Application of energy sources is discussed in greater detail above. In some embodiments, the energy source is applied in a non-invasive manner from outside the body. For example, as discussed above, an MRI device is useful for applying an amount of a magnetic field and/or RF pulse energy sufficient to adjust the valve implant 100. In some embodiments, the energy source is applied internally, for example, by surgically inserting a catheter into the body and applying energy through the catheter.

In some embodiments, the adjustment is performed in a single step. In certain embodiments, the adjustment is performed in a plurality of steps. In some embodiments, the adjustment steps are remote in time, which is useful, for example, where the aortic valve enlarges after initial implantation of the valve implant 100. Those skilled in the art will understand that in some embodiments, different regions of the valve implant 100 are adjusted to different extents, or not adjusted at all. For example, in some embodiments, each of the adjustable rings 104 and 106 is independently adjusted.

Figure 1B:
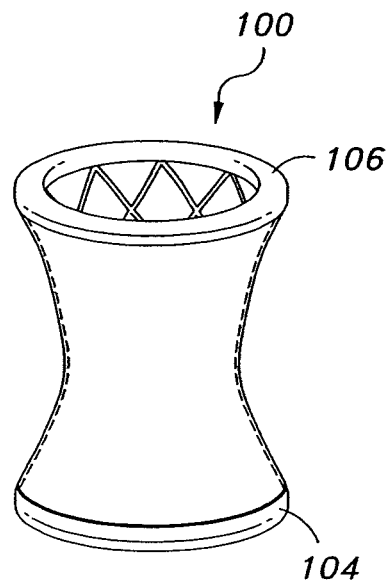
FIG. 1B illustrates the adjustable prosthetic valve implant of FIG. 1A in an adjusted state.

FIG. 1B illustrates the adjustable prosthetic valve implant 100 of FIG. 1A in an adjusted state according to certain embodiments. In the illustrated embodiment, each of the adjustable rings 104 and 106 has been adjusted to a larger diameter. Furthermore, the central region of the implant has maintained its original diameter. In certain embodiments, the central region may maintain its diameter due to the substantially rigid structure of the frame 114. In some embodiments, the central region may comprise an adjustable ring that maintains its original diameter while the other adjustable rings 104 and 106 expand in diameter.

Figure 1C:
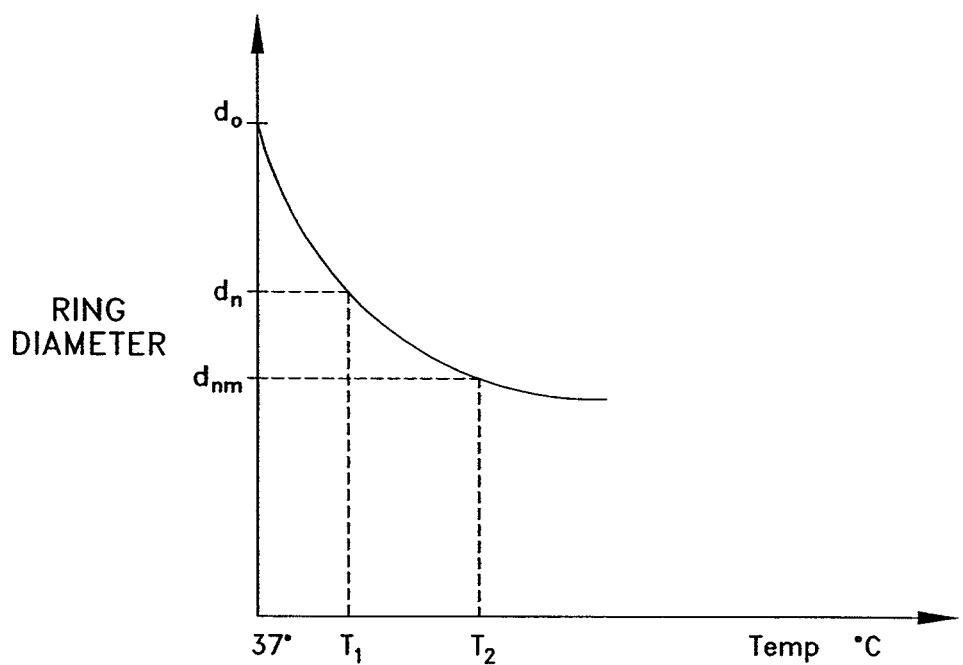
FIG. 1C is a graphical representation of the relationship between the change in diameter of an embodiment of an adjustable element and temperature.

The adjustment process, either non-invasive or using a catheter, is performed either all at once or incrementally in steps to achieve the desired amount of adjustment for producing the desired clinical result. If heating energy is applied such that the temperature of the adjustable element does not reach the $A_f$ temperature for a substantially maximum shape change, partial shape memory transformation occurs. FIG. 1C graphically illustrates the relationship between the temperature of an embodiment of a contractible adjustable element and its diameter or transverse dimension according to certain embodiments. At body temperature of approximately 37 degrees Celsius, the diameter of the adjustable element has a first diameter $d_o$. The shape memory material is then increased to a first temperature $T_o$. In response, the diameter of the adjustable element reduces to a second diameter $d_n$. The diameter of the adjustable element is then further reduced to a third diameter $d_{nm}$ by raising the temperature to a second temperature $T_2$.

As graphically illustrated in FIG. 1C, in some embodiments, the change in diameter from $d_o$ to $d_{nm}$, is substantially continuous as the temperature is increased from body temperature to $T_2$. For example, in some embodiments, a magnetic field of about 2.5 Tesla to about 3.0 Tesla is used to raise the temperature of the adjustable element above the $A_f$ temperature to complete the austenite phase transition and to return the adjustable element to the remembered configuration. In some embodiments, a magnetic field of about 2.0 Tesla to about 4.0 Tesla is used. In some embodiments, however, a lower magnetic field (e.g., 0.5 Tesla) is initially applied and increased (e.g., in 0.5 Tesla increments) until the desired level of heating and desired contraction of the adjustable element is achieved. In some embodiments, the adjustable element comprises a plurality of shape memory materials with different activation temperatures and the diameter of the adjustable element is reduced in steps as the temperature increases.

Whether the shape change is continuous or stepwise, the diameter or transverse dimension, or another dimension of the adjustable element is assessed and/or monitored in some embodiments during the adjustment process by MRI imaging, ultrasound imaging, computed tomography (CT), X-ray, or the like. In some embodiments, where magnetic energy is being used to activate an adjustable element, for example, MRI imaging is performed at a field strength that is lower than that required for activation of the adjustable element.

In some embodiments, one or more components and/or regions thereof of the valve implant 100 comprises a low friction coating, which facilitates insertion and placement of the device. For example, in some embodiments, a low friction coating is applied to at least a portion of each of the adjustable rings 104 and 106, the frame 114, or combinations thereof. The low friction coating comprises any suitable low friction coating known in the art, for example, fluorinated polymers, including EPTFE, PTFE (Teflon®), and the like. Other low friction coatings comprise lubricants known in the art, oils, and in particular non-toxic oils. In some embodiments, the low friction coating assists in removal of the device 100, if needed.

In certain embodiments, the prosthetic valve implant 100, upon activation, may change from a substantially linear (or "straight") shape to a substantially helical or substantially spiral shape. In certain embodiments, the change may occur to certain segments of the implant 100. In certain embodiments, the shape change may occur along the entire length of the implant 100.

Figure 1D:
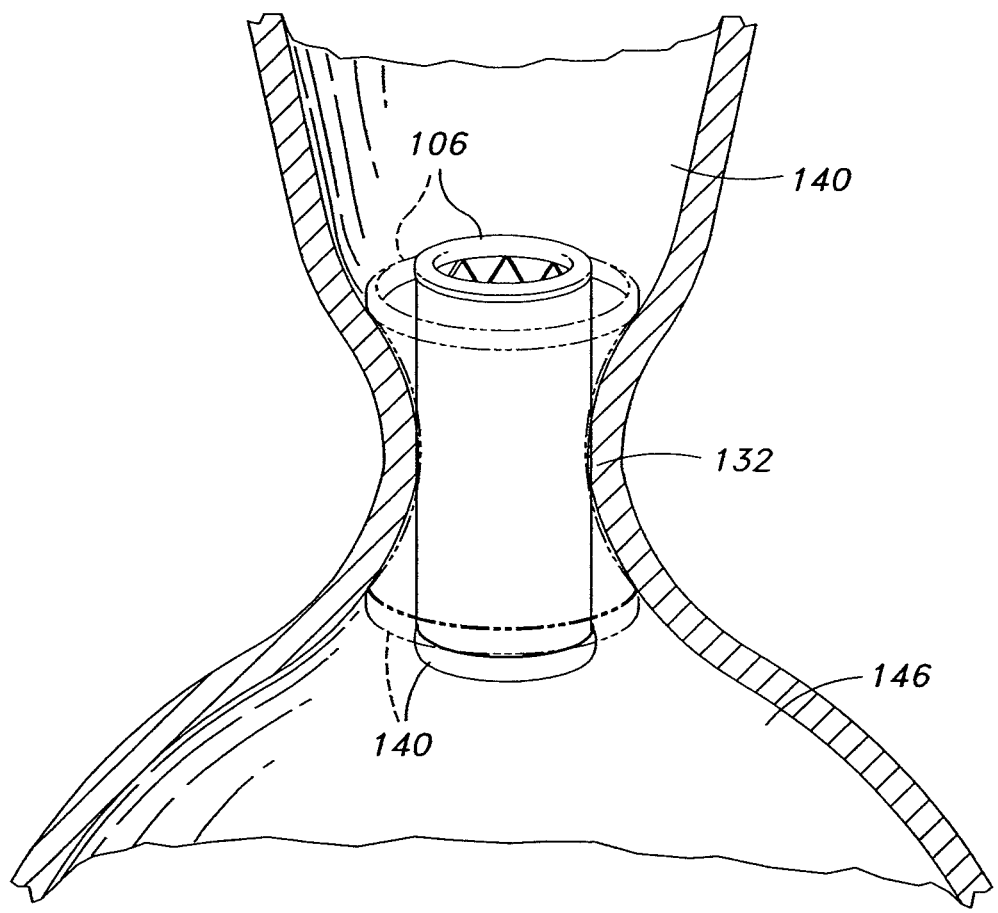
FIG. 1D depicts an adjustable prosthetic valve implant in a natural aortic valve position.

FIG. 1D depicts a prosthetic valve implant 100 of FIG. 1A deployed in a natural aortic valve position. In certain embodiments, the valve 100 may be implanted at a desired target location 132 in a body duct, for example, the aorta 140.

In certain embodiments, the valve implant 100 may delivered to a target location percutaneously in an antegrade (relative to the direction of blood flow) approach using a guide wire to gain access through the superior or inferior vena cava, for example, through groin access for delivery through the inferior vena cava. A guiding sheath can be advanced over the guide wire and into the inferior vena cava. The distal end of the guiding sheath can be passed through the right atrium and towards the septum. Once the distal end of the guiding sheath is positioned proximate to the septum, a needle or piercing member is preferably advanced through the guiding sheath and used to puncture the fossa ovalis or other portion of the septum. In some embodiments, the guiding sheath is dimensioned and sized to pass through the fossa ovalis without requiring a puncturing device. That is, the guiding sheath can pass through the natural anatomical structure of the fossa ovalis into the left atrium, and then into the left ventricle 146, where access to the aortic valve 132 may be achieved. In certain embodiments, the valve implant 100 may be delivered to a target location percutaneously using an retrograde (relative to the direction of blood flow) approach, where the aortic valve is approached from the descending aorta.

In certain embodiments, the valve 100 may be advanced while mounted over a balloon delivery device until it reaches the desired target location in a body duct 132. The balloon may then be inflated and the implant 100 may expand radially to take up its position, as illustrated. The prosthetic valve implant 100, which in certain embodiments comprises an artificial valve replacement in the central section of the implant 100, may thus replace the aortic valve 132 when implanted.

In certain embodiments, the adjustable prosthetic valve implant 100 of FIG. 1A may be adjusted after implantation. For example, as shown in phantom, the adjustable elements 106 and 104 at the proximal and distal ends of the implant may be adjusted to a larger diameter so as to abut the inner walls of the aorta 140 and left ventricle 146 respectively, in order to prevent or reduce post-surgical paravalvular leakage. In certain embodiments, the diameter of the central section of the implant 100 during implantation is configured to be substantially the same as the diameter of the aortic valve 132 after delivery to the target location 132. Furthermore, in certain embodiments, the central region of the implant may comprise an adjustable element which may be similarly adjusted in order to address post-surgical complications. In certain embodiments containing an adjustable element in the central section of the implant 100, the adjustable element of the central section may be adjusted post-operatively during a first procedure while the adjustable elements in the proximal and distal ends of the implant may be adjusted during a second post-operative procedure.

Figure 2A:
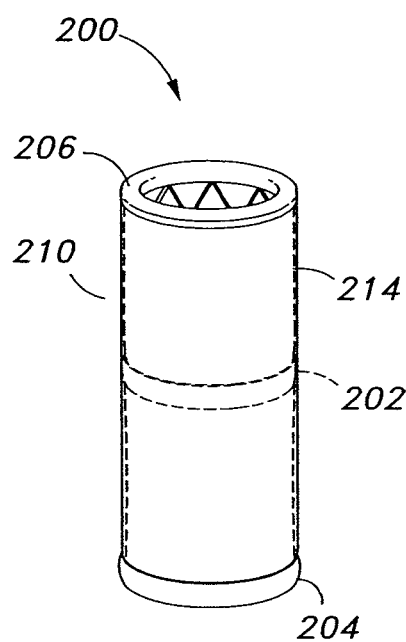
FIG. 2A illustrates another embodiment of a prosthetic valve implant.

FIG. 2A illustrates another embodiment of the prosthetic valve implant 200 that is similar to the embodiment illustrated in FIG. 1A. The prosthetic valve implant 200 comprises an additional adjustable ring substantially equidistant from the adjustable rings 204 and 206 located at the distal and proximal ends of the implant, respectively. The construction and materials for this embodiment are substantially similar as described above for the embodiment illustrated in FIG. 1A.

In the illustrated embodiment, the body 210 comprises one or more adjustable elements, which permit the shape of the body 210 to be adjusted post implantation. In the illustrated embodiment, the adjustable elements 202, 204, and 206 are disposed at the center and the ends of the implant 200. Those skilled in the art will understand that other configurations are possible. The adjustable elements are, for example, shaped memory materials in the form of rings, wires, bands, strips, and the like. In the illustrated embodiment, the adjustable elements 202, 204, and 206 are integrated with the frame 214. In certain embodiments, the adjustable elements 202, 204, and 206 are separate from the frame 214.

Figure 2B:
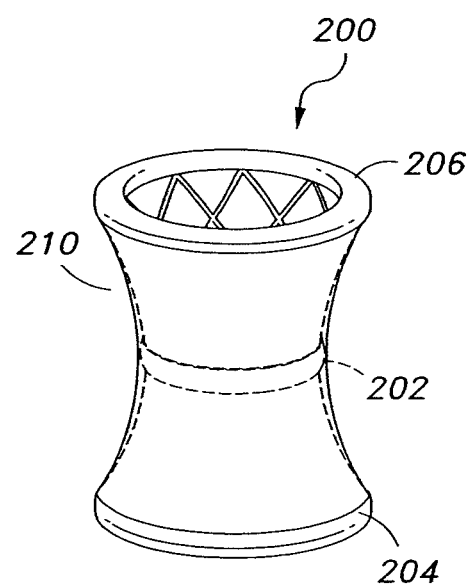
FIG. 2B illustrates the prosthetic valve implant of FIG. 2A after adjustment.

FIG. 2B illustrates the prosthetic valve implant 200 of FIG. 2A after activation. In the illustrated embodiment, expanding the adjustable elements 202, 204, and 206 causes the shape of the prosthetic valve implant 200 to change. Adjustable rings 204 and 206 have been expanded, while adjustable ring 202 has contracted. Consequently, the central region of the implant 200 has contracted radially and the end regions have expanded radially. In some embodiments, the maximum diameter of the expanded portion is from about 5 cm to about 8 cm. In some embodiments, the minimum diameter of the contracted portion is from 0.25 to 0.5 cm.

Figure 3A:
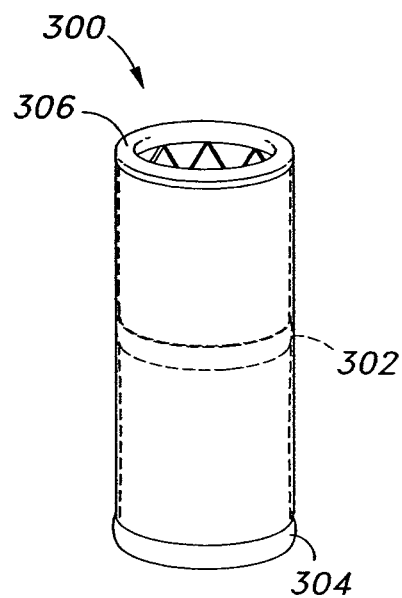
FIG. 3A illustrates another embodiment of the prosthetic valve implant.

FIG. 3A illustrates another embodiment of the prosthetic valve implant 300 that is similar to the embodiment illustrated in FIG. 2A. The prosthetic valve implant 300 comprises expanding adjustable elements 302, 304, and 306. Adjustable rings 304 and 306 are located at the ends of the implant 300, while adjustable ring 306 is located in the central region of the implant 300. The construction and materials for this embodiment are substantially similar as described above for the embodiment illustrated in FIG. 1A.

Figure 3B:
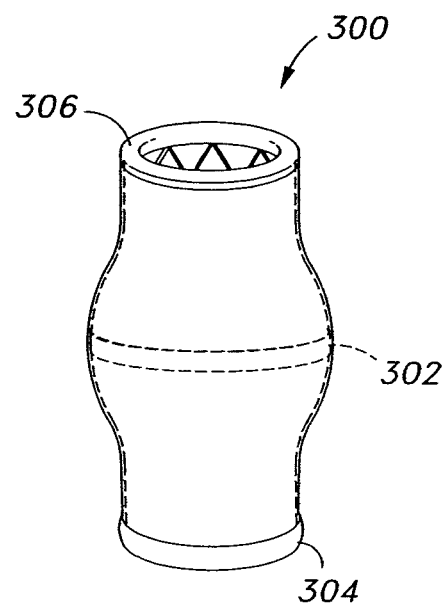
FIG. 3B illustrates the prosthetic valve implant of FIG. 3A after activation of the central region adjustable ring.

FIG. 3B illustrates the prosthetic valve implant 300 of FIG. 3A after activation of the adjustable ring 302 located in the central region of the implant 300. The adjustable ring 302 has expanded radially. The other two adjustable rings, 304 and 306, have not been activated, and therefore maintain their original shape. Expanding the adjustable ring 302 causes the central region of the adjustable implant 300 to also expand. The end regions, however, have maintained their original shape, as discussed above.

Figure 3C:
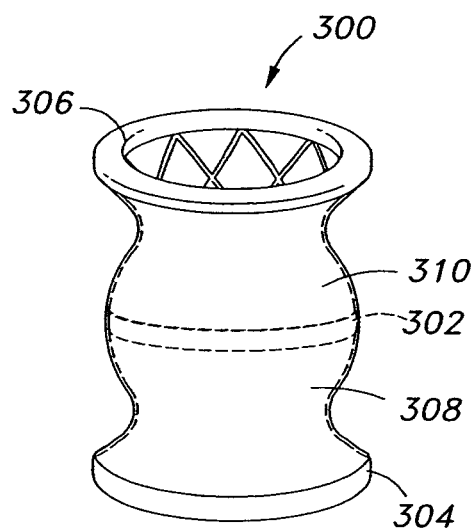
FIG. 3C illustrates the prosthetic valve implant of FIG. 3A after activation of all adjustable rings.

However, when adjustable rings 304 and 306, which are located at the ends of the implant 300, are activated, the rings 304 and 306 expand radially, causing the end regions of the implant 300 to also expand radially, as illustrated in FIG. 3C. Certain areas of the implant 300 nonetheless maintain substantially the same original diameter, such as the two bands 310 and 308 located substantially equidistant between each either end ring 304 and 306 and the central ring 302. However, in some embodiments, expanding all rings in an implant may cause the entire implant to expand without any portion maintaining its original radius.

Figure 4A:
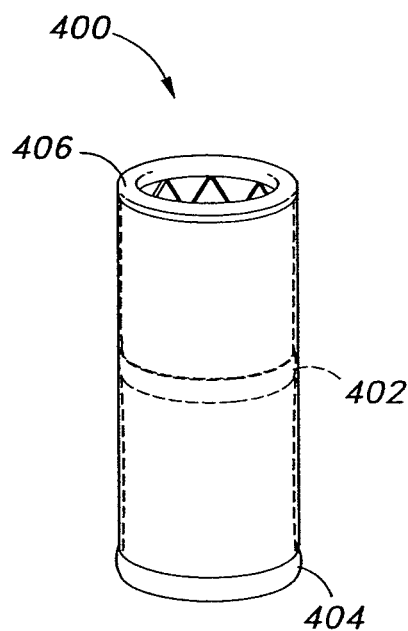
FIG. 4A illustrates another embodiment of the prosthetic valve implant.

FIG. 4A illustrates another embodiment of the prosthetic valve implant 400 that is similar to the embodiment illustrated in FIG. 2A. The prosthetic valve implant 400 comprises expanding adjustable elements 402, 404, and 406. Adjustable rings 404 and 406 are located at the ends of the implant 400, while adjustable ring 406 is located in the central region of the implant 400. The construction and materials for this embodiment are substantially similar as described above for the embodiment illustrated in FIG. 1A.

Figure 4B:
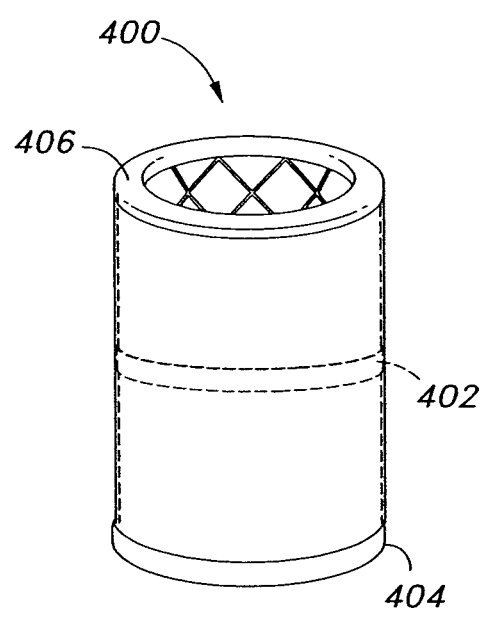
FIG. 4B illustrates the prosthetic valve implant of FIG. 4A after activation of adjustable rings located in the central and end regions of the implant.

FIG. 4B illustrates the prosthetic valve implant 400 of FIG. 4A after activation of adjustable rings 402, 404, and 406 located in the central and end regions of the implant 400. Each of the adjustable rings 402, 404, and 406 has expanded radially, causing the entire implant to expand radially without any portion maintaining its original radius.

Figures 5A, 5B:
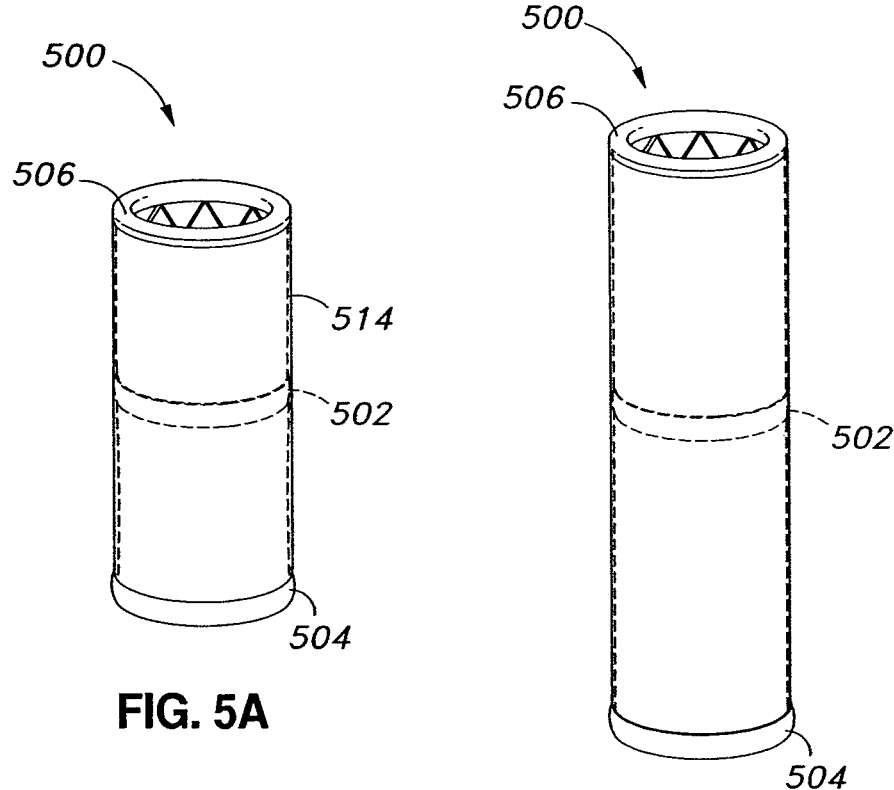
FIG. 5A illustrates another embodiment of the prosthetic valve implant.
FIG. 5B illustrates the prosthetic valve implant of FIG. 5A after activation.

FIG. 5A illustrates another embodiment of the prosthetic valve implant 500 that is similar to the embodiment illustrated in FIG. 2A, except that when activated, the adjustable portions of the implant 500 expand in the axial, or longitudinal, direction, instead of radially. The prosthetic valve implant 500 comprises expanding adjustable elements 502, 504, and 506. Adjustable rings 504 and 506 are located at the ends of the implant 500, while adjustable ring 506 is located in the central region of the implant 500. The implant 500 further comprises an adjustable frame 514 element, which may adjust the length of the implant 500 to a longer length. The construction and materials for this embodiment are substantially similar as described above for the embodiment illustrated in FIG. 1A.

FIG. 5B illustrates the prosthetic valve implant 500 of FIG. 5A after activation. In some embodiments, activation of the adjustable material provides a decrease in length. In some embodiments, activation of the adjustable material provides an increase in length, as illustrated. The frame element 514 has been adjusted to a greater longitudinal length. In certain embodiments, length change may be effected using any shape memory material described above, such as nitinol. In some embodiments, the change in length is from about 5% to about 25%. In some embodiments, the diameter of the adjustable portion also changes, for example, increases, on adjustment, either by adjusting the frame 514 or the adjustable rings 502, 504, and 506.

Figure 6:
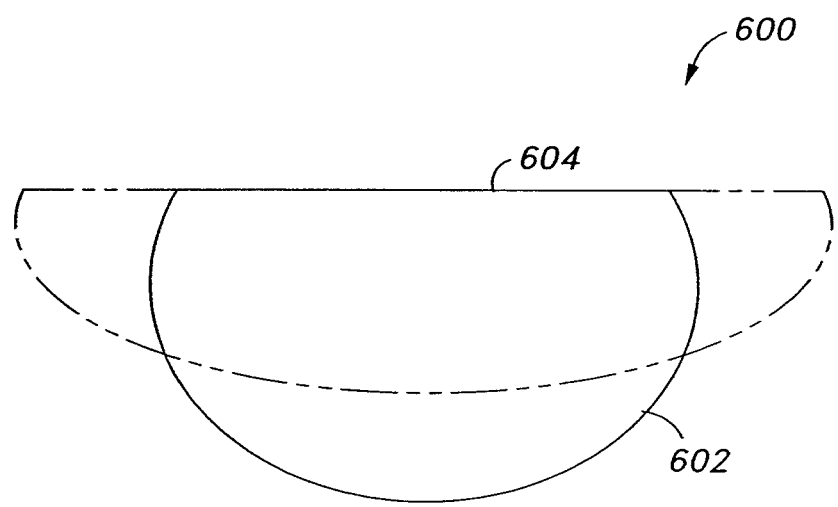
FIG. 6 illustrates a lateral view, looking along the flow path, of an embodiment of a prosthetic valve implant having a "D" shape.

FIG. 6 illustrates a lateral view, looking along the flow path, of another embodiment of a prosthetic valve implant 600 having a "D" shape that is adjustable after implantation. The implant 600 is illustrated in an unadjusted configuration in solid lines, and in an adjusted configuration in phantom. The implant 600 comprises a substantially flat edge 604 and a substantially arcuate edge 602. In certain embodiments, the flat edge 604 can be continuous. In certain embodiments, the flat edge 604 may comprise a break or discontinuity.

In certain embodiments, the implant 600 may be fabricated from shape-memory materials, as described above. For example, in certain embodiments, the frame may comprise shape memory materials, such as nitinol. In certain embodiments, the implant 600 may be configured to have a post-actuation shape when the temperature is raised above the $A_f$ temperature. In certain embodiments, the implant 600 may be comprised of multiple elements, at least one of which comprises a shape memory material. Each shape memory element may be configured to have different activation temperatures and austenitic shapes. In certain embodiments, the implant 600 is fabricated from wire, tubing, flat wire, "U" channel or the like. In certain embodiments, the implant 600 may further comprise elements such as a tube with an internal wire, multiple laminated flat wires, or the like.

Upon adjustment of the prosthetic valve implant 600, the substantially straight section 604 extends in length while the height of the substantially arcuate section 602 decreases. In certain embodiments, which have no break in continuity on the flat side 604, as illustrated, the circumference of the implant 600 may remain substantially unchanged. In certain embodiments where there is a break in continuity on the flat side 604, the circumference of the implant may change.

Figure 7:
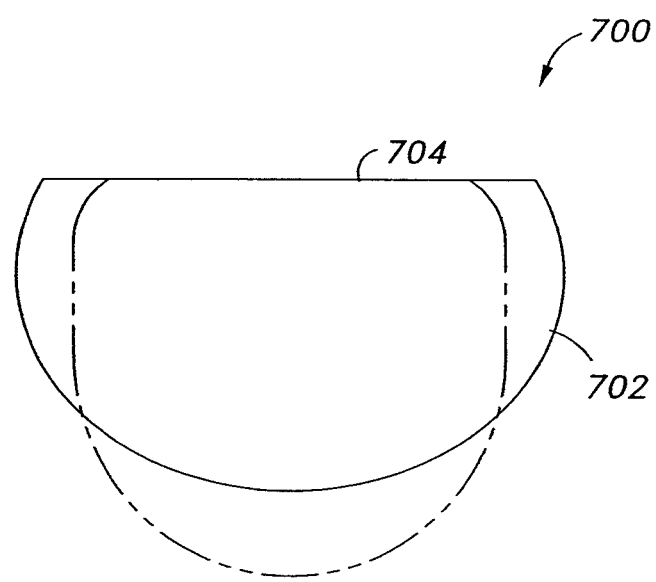
FIG. 7 illustrates a lateral view, looking along the flow path, of another embodiment of a prosthetic valve implant having a "D" shape.

FIG. 7 illustrates a lateral view, looking along the flow path, of another embodiment of a prosthetic valve implant 700 having a "D" shape that is adjustable after implantation. The implant 700 is illustrated in an unadjusted configuration in solid lines, and in an adjusted configuration in phantom. The construction and materials for this embodiment are substantially similar as described above for the embodiment illustrated in FIG. 6.

Upon adjustment of the prosthetic valve implant 700, the substantially straight section 704 decreases in length while the height of the substantially arcuate section 702 increases. In certain embodiments which have no break in continuity on the flat side 704, as described above and as illustrated in FIG. 7, the circumference of the implant 700 may remain substantially unchanged.

Figure 8:
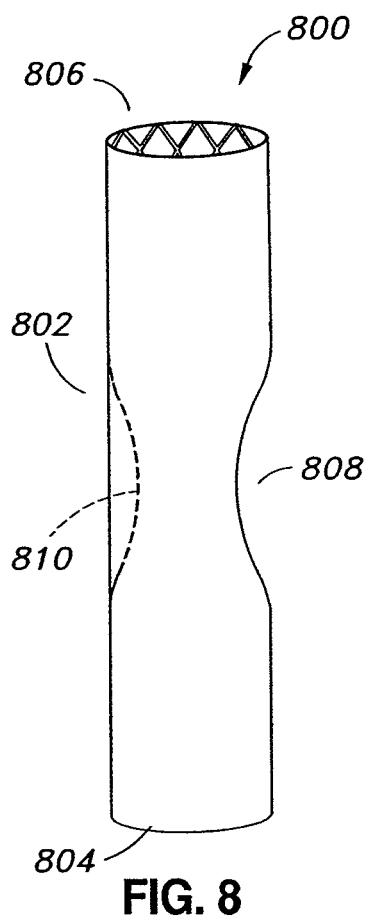
FIG. 8 illustrates a side view of another embodiment of a prosthetic valve implant.

FIG. 8 illustrates a side view of an embodiment of a prosthetic valve implant 800 according to certain embodiments. The implant 800 is illustrated in an unadjusted configuration in solid lines, and in an adjusted configuration in phantom. The central region 802 of the implant 800 comprises an inward depression 808 on one side. The construction and materials for this embodiment are substantially similar as described above for the embodiment illustrated in FIG. 6. Upon adjustment of the prosthetic valve implant 800, the central region 802 comprises a plurality of inward depressions 808. In certain embodiments, the inward depressions 810 may be bilateral. In certain embodiments, the inward depressions 810 may be asymmetric. In certain embodiments, the inward depressions 810 which result from the adjustment may result in a circumferential groove or depression. In certain embodiments, the upstream end 806 portion and the downstream end 804 portion remain unaffected by the adjustment.

Figure 9:
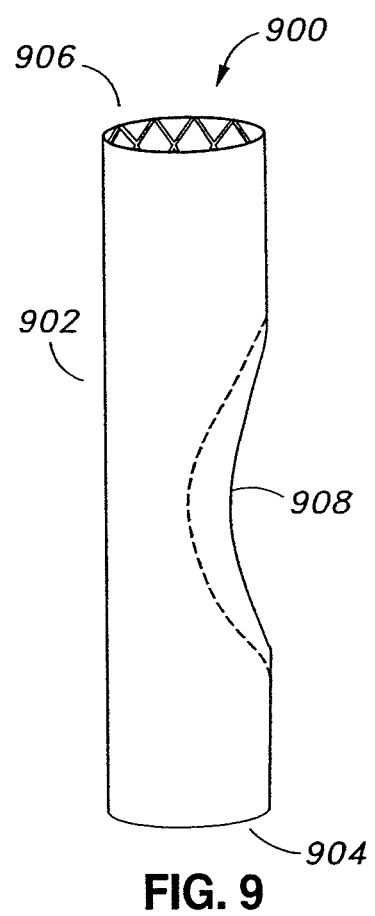
FIG. 9 illustrates a side view of another embodiment of a prosthetic valve implant.

FIG. 9 illustrates a side view of an embodiment of a prosthetic valve implant 900 according to certain embodiments. The implant 900 is illustrated in an unadjusted configuration in solid lines, and in an adjusted configuration in phantom. The central region 902 of the implant 900 comprises an inward depression 908 on one side, similar to the embodiment 800 illustrated in FIG. 8. The construction and materials for this embodiment are substantially similar as described above for the embodiment illustrated in FIG. 6. Upon adjustment of the prosthetic valve implant 900, the depression 908 increases in depth and width. The depression 908 in the side of the implant 900 in its adjusted shape has become substantially larger than in the unadjusted configuration. In certain embodiments, the upstream end 906 portion and the downstream end 904 portion remain unaffected by the adjustment.

Figures 10A, 10B:
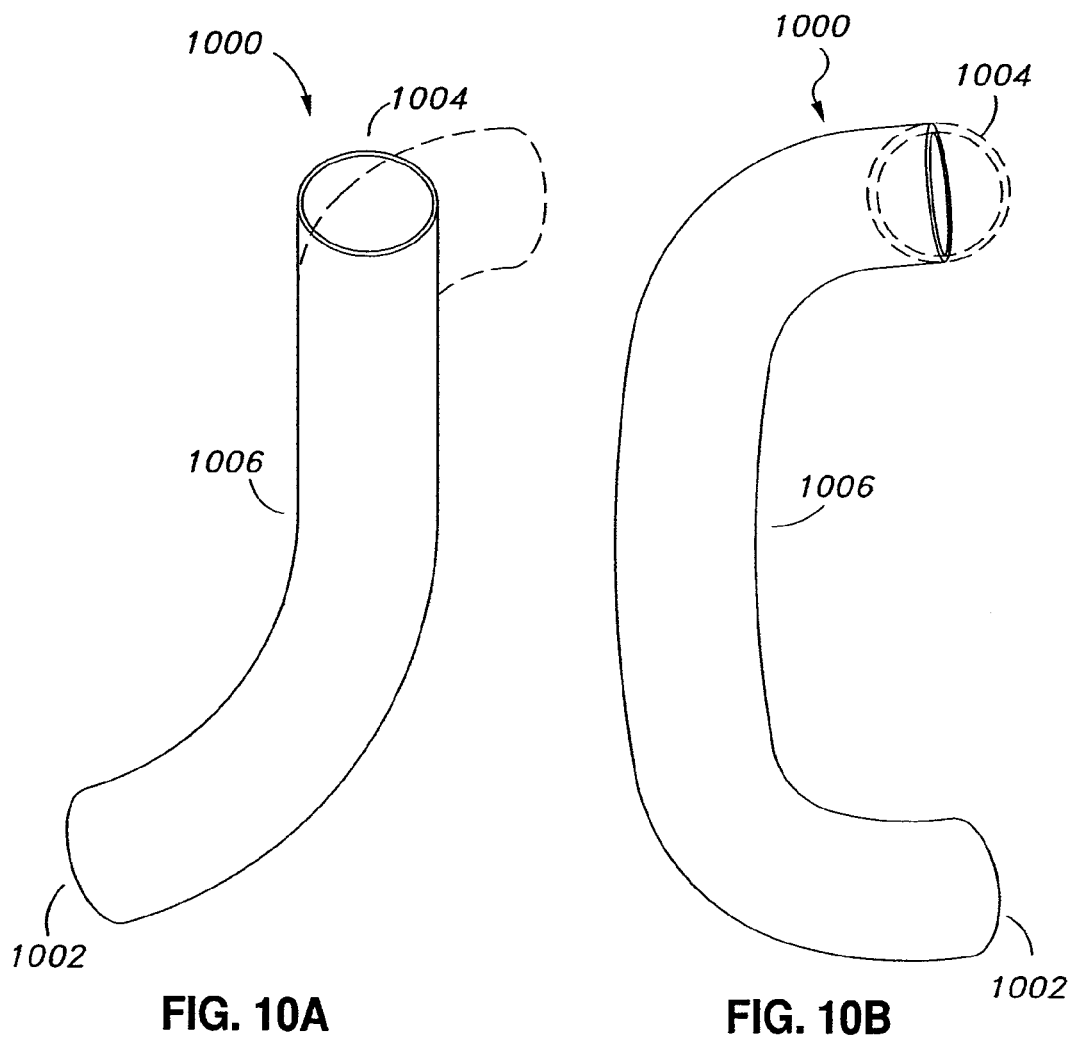
FIG. 10A illustrates a first side view of an embodiment of an unadjusted implant having a "C"-shaped configuration.
FIG. 10B illustrates a second side view of the C-shaped implant of FIG. 10A.

Although the embodiments of the adjustable prosthetic valve implant described so far are substantially linear, in certain embodiments the implant may take any other shape. For example, FIG. 10A illustrates a first side view of an unadjusted implant 1000 having a "C"-shaped configuration and comprising a first end 1004, a central region 1006, and a second end 1002. The implant 800 is illustrated in an unadjusted configuration in solid lines, and in an adjusted configuration in phantom. In the illustration, the second end 1002 of the implant 1000 is deflected out of the plane of the "C." FIG. 10B illustrates a second side view of the C-shaped implant 1000 of FIG. 10A. From this view, the implant 1000 has a C-shape appearance.

Upon activation, the first end 1004 of the prosthetic valve implant 1000 is deflected out of the place of the "C." Consequently, after activation, both the first end 1004 and the second end 1002 of the "C" are deflected in opposite directions out of the plane of the "C". The curved region 1006 remains substantially within the original unadjusted plane, thus retaining the C-shape of the implant 1000.

Figure 11A:
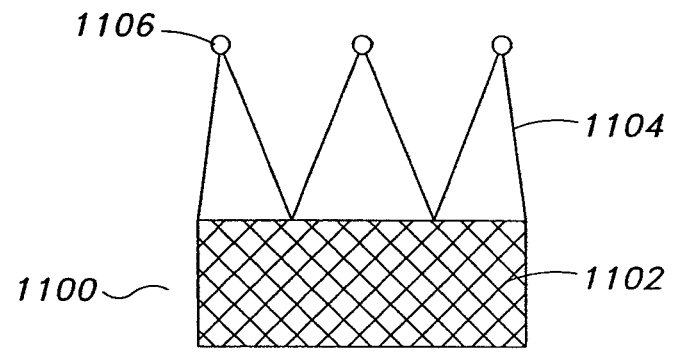
FIG. 11A illustrates a side view of an embodiment of an unadjusted prosthetic valve implant comprising a three-post crown support.

FIG. 11A illustrates a side view of an unadjusted prosthetic valve implant 1100 comprising a three-post crown support 1104 near a central valve, a base ring structure 1102 and a plurality of attachment posts 1106. The construction and materials for this embodiment are substantially similar as described above for the embodiment illustrated in FIG. 1. The illustrated implant 1100 is suitable for structurally housing a prosthetic valve, such as a trileaflet tissue valve. The crown support 1114 may allow for safe attachment of the implant 1100 to a valve by means of stitching or other suitable attachment method. In certain embodiments, the crown support 1114 may be connected to at least one end of the adjustable prosthetic valve implant in order to beneficially increase holding capabilities within the cardiovascular system when adjusted.

Figure 11B:
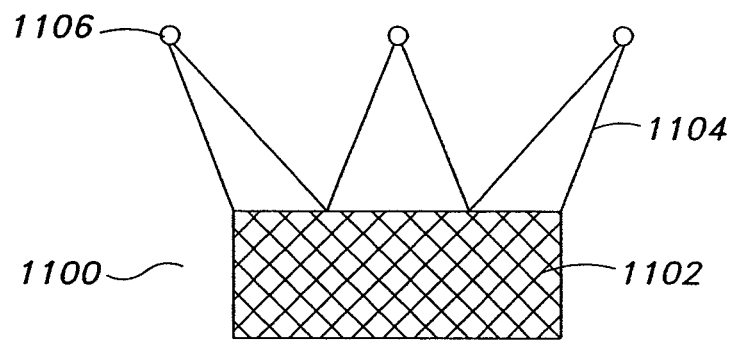
FIG. 11B illustrates a side view of the adjusted implant of FIG. 11A when activated.

FIG. 11B illustrates a side view of the adjusted implant 1100 of FIG. 11A when activated. Upon activation, the attachment points 1106 and crown structures 1104 deflect radially outward. In certain embodiments, deflection may also occur in the radially inward direction.

Figure 11C:
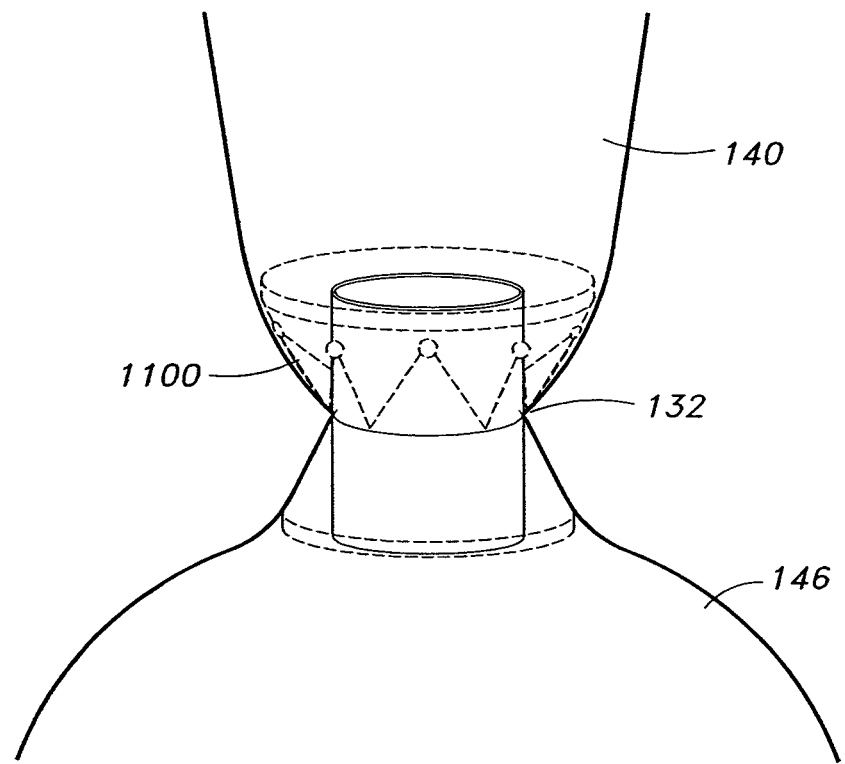
FIG. 11C illustrates a side view of the implant of FIG. 11A attached to the central section of the adjustable prosthetic valve implant of FIG. 1A and deployed in a natural aortic valve position.

FIG. 11C illustrates a side view of the implant 1100 of FIG. 11A attached to the central section of the adjustable prosthetic valve implant 100 of FIG. 1A and deployed in a natural aortic valve position. The addition of the crown implant 1100 to the prosthetic valve implant may increase the holding capacity of the prosthetic valve implant in the aortic valve 132 when adjusted, as shown in phantom.

Figure 12A:
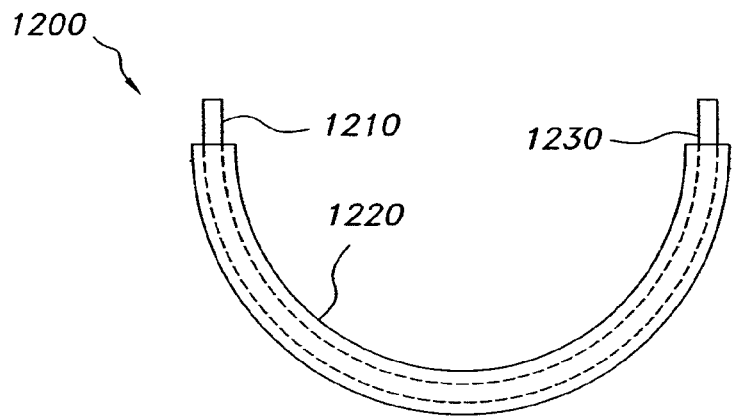
FIG. 12A illustrates a top view of an embodiment of an adjustable element comprising an coating layer.

FIG. 12A illustrates an embodiment of an adjustable element 1200 comprising a U-shaped shape memory element 1210 on which is disposed a coating or layer 1220. As discussed above, suitable coatings include thermally insulators, electrical insulators, energy absorbing materials, porous materials, lubricating materials, bioactive materials, biodegradable materials, combinations thereof, and the like. In the illustrated embodiment, the layer and/or jacket 1220 is a thermal insulation layer, for example, a polymer layer. A portion of the insulating layer 1230 remains exposed in the illustrated embodiment. In some embodiments, the insulating layer 1230 also serves another function, for example, as a HIFU absorbing material, a MRI absorbing material, a lubricating layer, a drug eluting layer, a biodegradable layer, a porous layer, and combinations thereof.

Figure 12B:
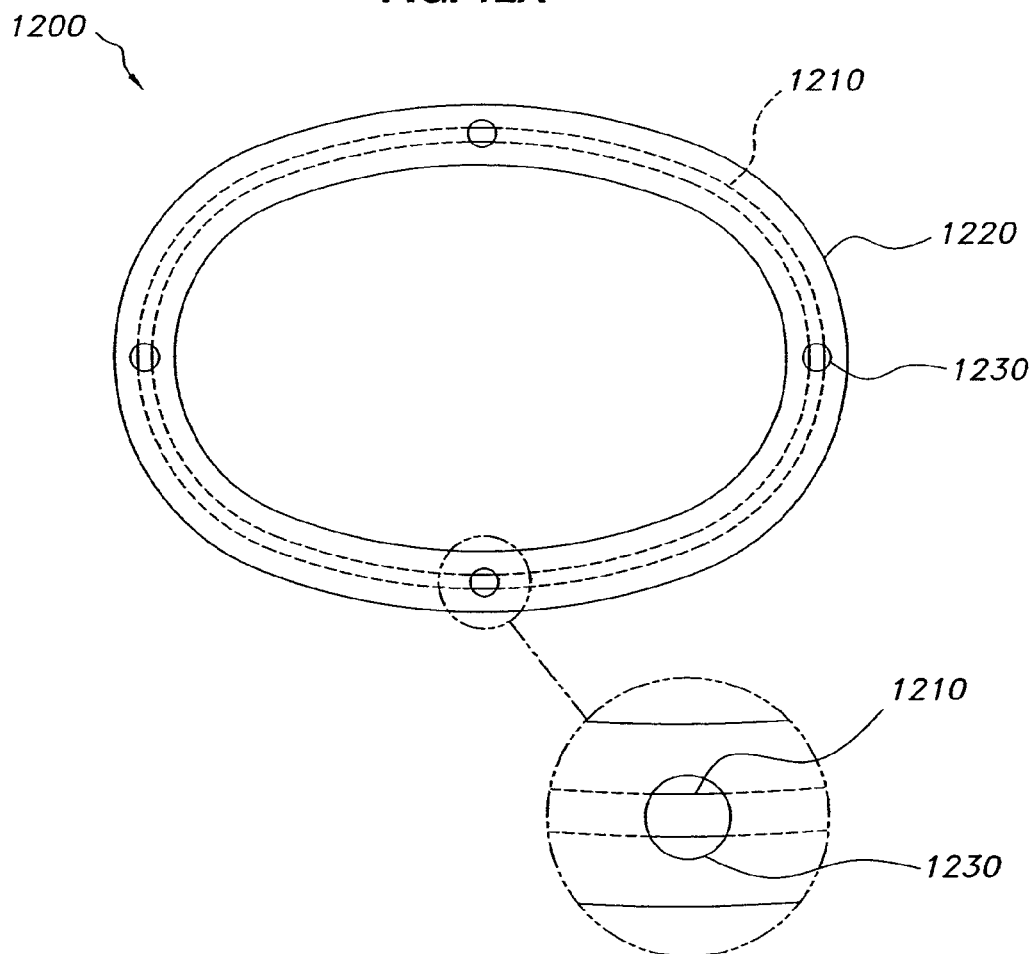
FIG. 12B illustrates another embodiment of an adjustable element comprising an coating layer.
Figure 12C:
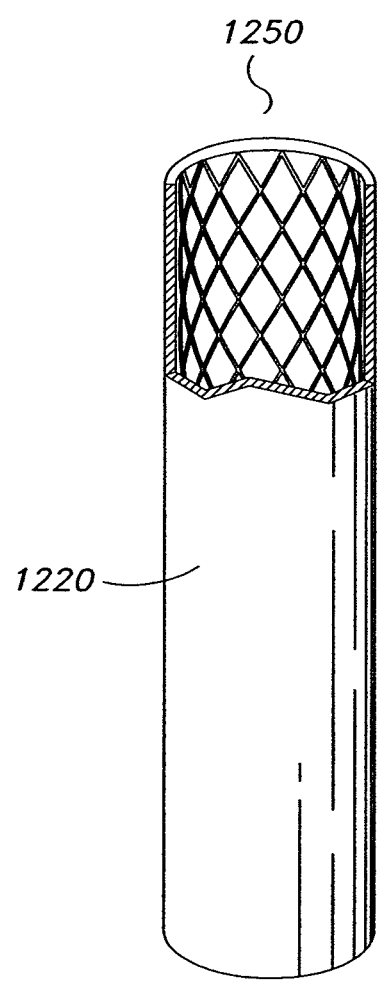
FIG. 12C illustrates a side, partial breakaway view of an unadjusted implant comprising an energy absorbing coating on its exterior surface.

FIG. 12B illustrates another embodiment in which the shape memory element 1210 is a ring. A plurality of windows 1230 are provided in the insulation layer 1220. In these embodiments, the insulation layer reduces heat loss, thereby facilitating activation of the shape memory element. FIG. 12C illustrates a side, partial breakaway view of an unadjusted implant 1250 comprising an energy absorbing coating 1220 on its exterior surface.

Figure 13A:
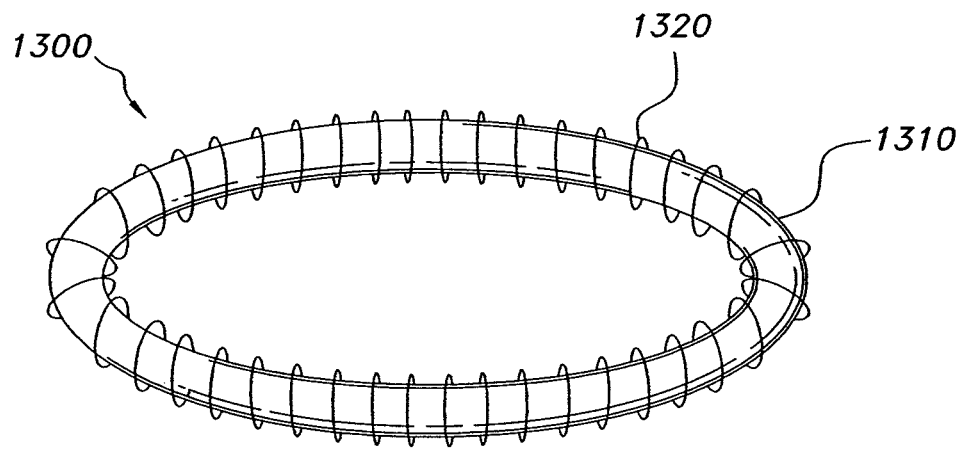
FIG. 13A illustrates a perspective view of an adjustable element comprising a wire wrapping.

In the embodiment illustrated in FIG. 13A, an adjustable element 1300 comprises a ring-shaped shape memory element 1310 and a fine wire 1320 wrapped thereon. The fine wire 1320 is any suitable conductive wire, for example, platinum coated copper, titanium, tantalum, stainless steel, gold, and combinations thereof. As discussed above, in some embodiments, the wire 1320 forms a loop suitable for inductive heating. The fine wire 1320 permits focused and/or rapid heating of the adjustable element 1300 using, for example, by induction, while reducing heating of surrounding tissue. The fine wire 1320 is from about 0.05 mm to about 0.5 mm in diameter. Those skilled in the art will understand that different wrapping geometries are also useful, for example, circumferential and/or wrapping on a bias. Some embodiments comprise additional wrapped wire, for example, in additional layers, or disposed at selected portions of the adjustable element. As discussed above, some embodiments comprise a thermally insulating, electrically insulating, protective, and/or covering layer.

Figure 13B:
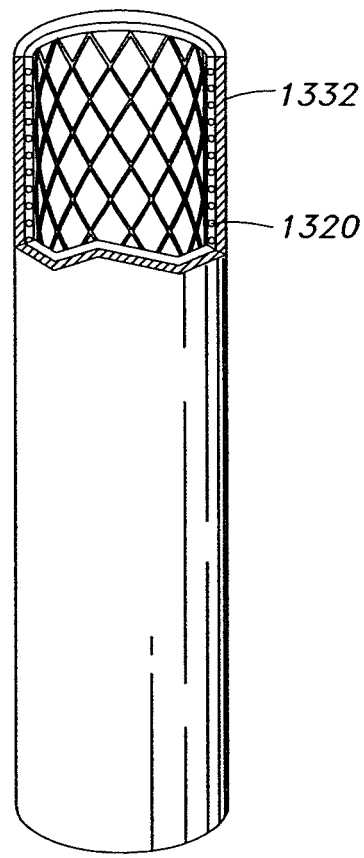
FIG. 13B illustrates a side, partial breakaway view of an unadjusted implant comprising a fine wire on the exterior surface of its outer wall.

FIG. 13B illustrates a side, partial breakaway view of an unadjusted implant comprising a fine wire 1320 on the exterior surface of its outer wall 1328. The wire 1320 may be wrapped around the expandable and contractible shape memory wall comprising the implant 1350 in a fashion similar to that used to wrap the adjustable element in FIG. 13A. In certain embodiments, the wire 1320 may further be combined and layered under, or over, the energy absorbing coating 1220, detailed in FIGS. 12A-12C. In certain embodiments, an insulating layer 1322 can be disposed exterior to the heating coil 1320 to minimize heat transfer to surrounding tissue.

In some embodiments, the adjustable elements in the graft implant are activated using one or more purpose built devices which are positioned on or around a patient's body in such a way to focus the energy on the adjustable elements. In some embodiments, the purpose built device is wrapped around the patient.

Figure 14A:
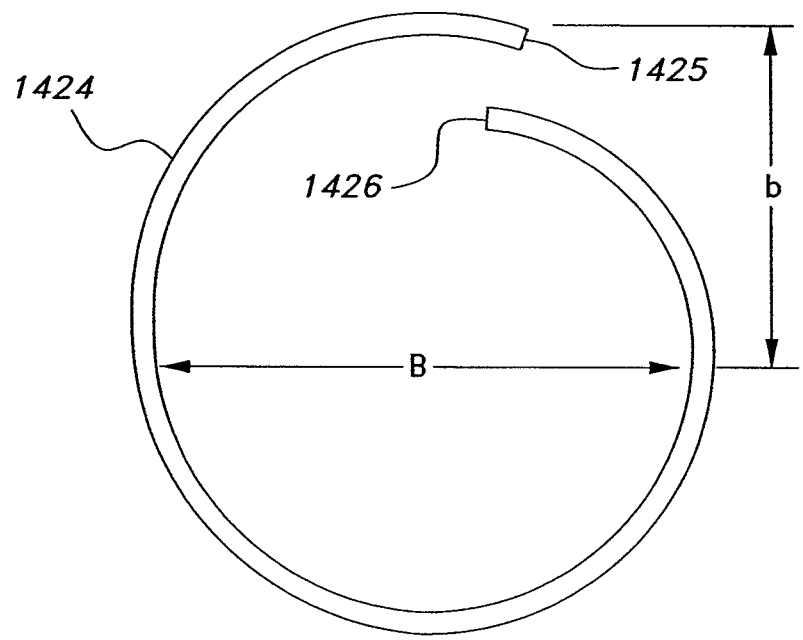
FIG. 14A illustrates a top view of an embodiment of an adjustable element or ring that is not closed.
Figure 14B:
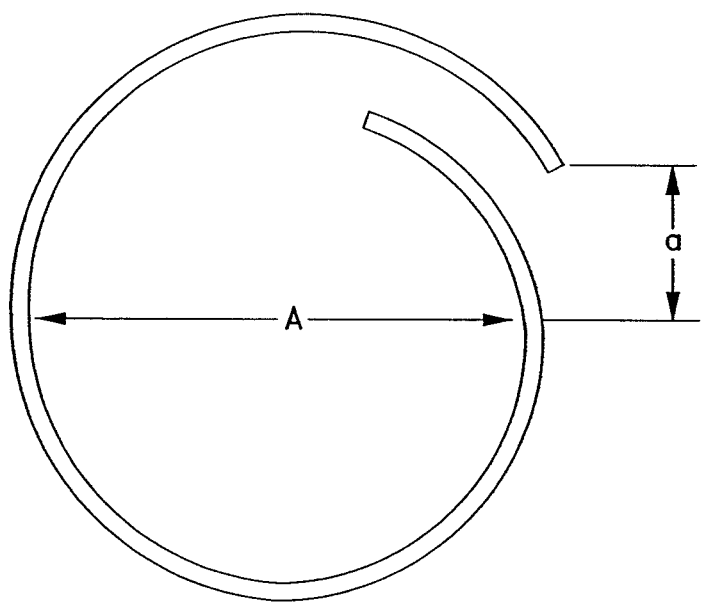
FIG. 14B illustrates the adjustable element of FIG. 14A after adjustment.

FIG. 14A illustrates an embodiment of an adjustable ring and/or adjustable element 1424, which is expandable and/or contractible upon activation. The adjustable ring 1424 does not form a closed shape. That is, the adjustable ring 1424 comprises a first end 1425 and a second end 1426 that do not contact, thereby forming a C-shaped and/or G-shaped structure. In the illustrated embodiment, the adjustable ring 1424 is substantially flat. In certain embodiments, the adjustable ring 1424 is not flat. FIG. 14B illustrates the adjustable ring 1424 of FIG. 14A after activation. In the illustrated embodiment, the adjustable ring 1424 contracts on activation. The dimension B in FIG. 14B is less than the corresponding dimension A FIG. 14A, and the dimension b in FIG. 14B is less than the corresponding dimension a in FIG. 14A. Those skilled in the art will understand that in certain embodiments, the adjustable ring 1424 expands on activation.

Figure 15:
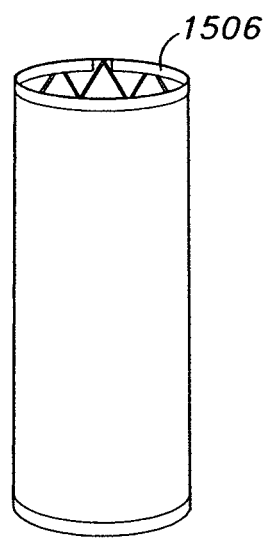
FIG. 15 illustrates in perspective view an embodiment of an adjustable prosthetic valve implant comprising the adjustable element of FIG. 14A.

FIG. 15 illustrates an embodiment of a prosthetic implant 1500 that is similar to the embodiment illustrated in FIG. 1A, in which the adjustable ring 1506 is similar to the adjustable ring illustrated in FIG. 14A.

Figure 16A:
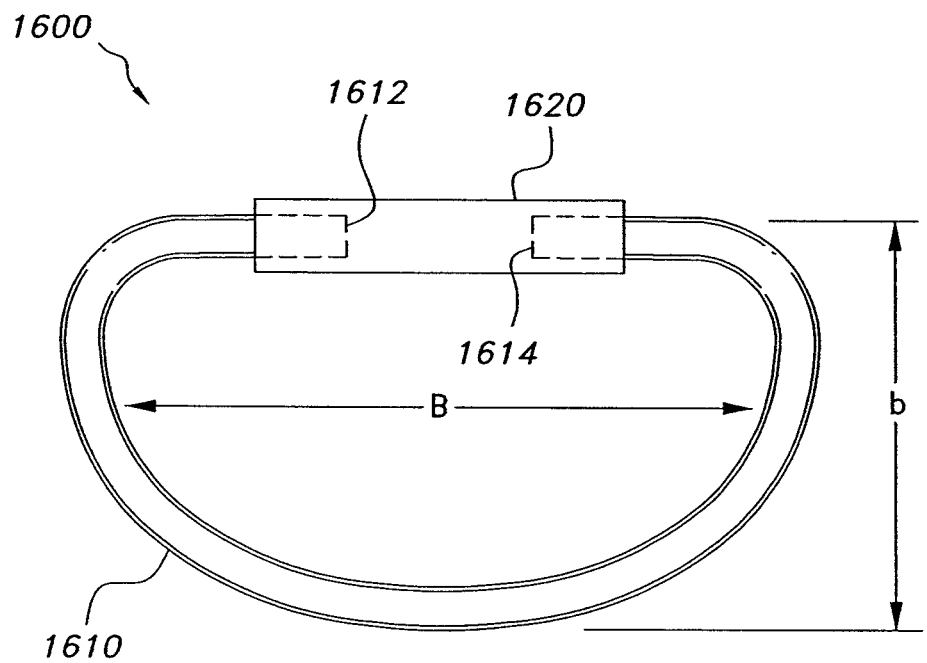
FIG. 16A illustrates a top view of an embodiment of an adjustable element comprising a ratchet.
Figure 16B:
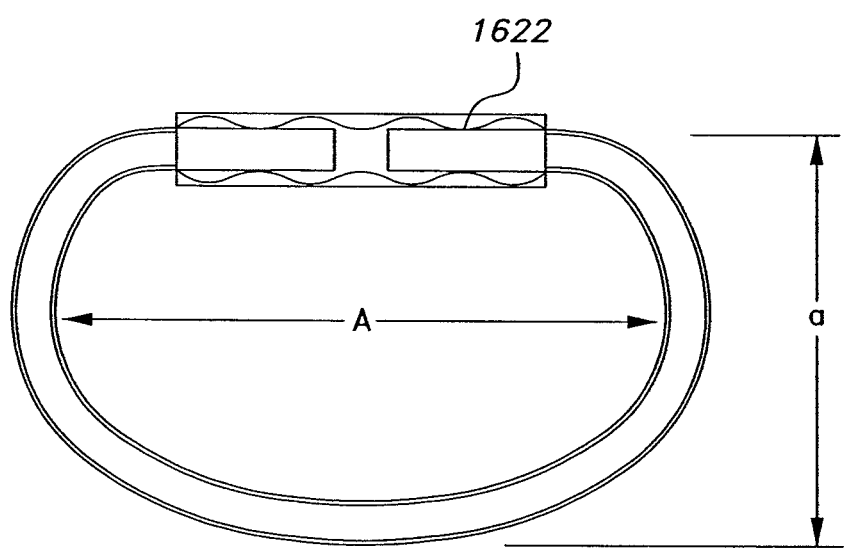
FIG. 16B illustrates a top view of another embodiment of an adjustable element comprising a ratchet.

Another embodiment of an adjustable ring and/or adjustable element 1000 is illustrated in FIG. 16A comprising a ring member 1610 and a ratchet member 1620. In the illustrated embodiment, the ends of the ring member 1612 and 1614 are disposed within the ratchet member 1620. The ratchet prevents undesired size changes in the adjustable element, caused, for example, by pulsatile dilation and contraction of the aorta, common iliac arteries, and/or AAA. Suitable ratchet mechanisms are known in the art. An embodiment of the ratchet member 1620 is illustrated in cross-section in FIG. 16B. The ratchet member 1620 comprises internal gripping elements 1622 which permit one-way motion of the ends of the ring member 1612 and 1614 therein. The ring member 1610 comprises a shaped memory material, for example, nitinol. The adjustable ring 1600 is expandable and/or contractible on activation. For example, the dimensions A and a in the activated configuration (FIG. 16B) are larger than the dimensions B and b in the unactivated configuration (FIG. 16A) in some embodiments and are smaller in some embodiments. In certain embodiments, one of the dimensions is larger post-activation, and the other is smaller. In certain embodiments, one of the dimensions substantially does not change on activation. In some embodiments, the entire ring member 1610 is a shape memory material, for example, nitinol, while in certain embodiments, the ring member 1610 comprises a material other than a shaped memory material. For example, in some embodiments, the ring member 1610 is a composite.

Figure 17A:
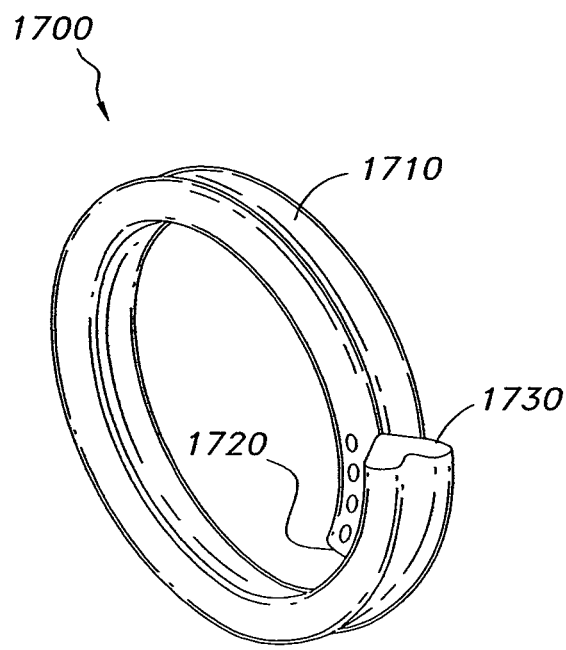
FIG. 17A illustrates in perspective view an embodiment of a spiral adjustable element comprising a groove.
Figure 17B:
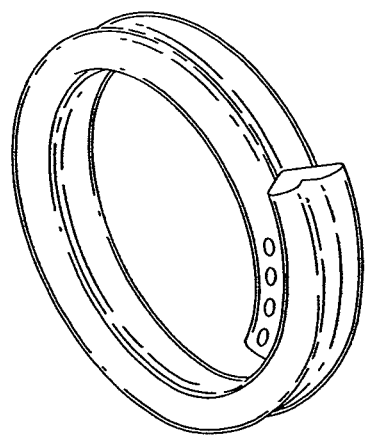
FIGS. 17B and 17C illustrate steps in the adjustment of the adjustable element of FIG. 17A.
Figure 17C:
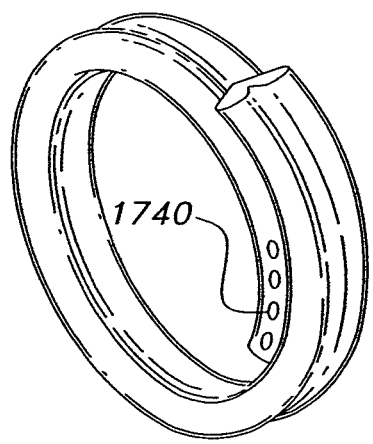

FIG. 17A illustrates another embodiment of an adjustable ring and/or adjustable element 1700 comprising a groove 1710 disposed along the outer periphery of the ring 1700. The adjustable element 1700 comprises a first end 1720, which in the illustrated embodiment, is an inner end, and a second end 1730, which in the illustrated embodiment is an outer end. In the illustrated embodiment, adjustable ring 1700 contracts upon activation as illustrated in FIG. 17B and FIG. 17C. As illustrated in the sequence of FIGS. 17A-17C, the groove 1710 guides the first and second ends 1720 and 1730, thereby maintaining a substantially planar configuration. In some embodiments, the adjustable ring 1700 expands on activation, for example, in the sequence of FIGS. 17C-17A. Those skilled in the art will understand that in some embodiments, the groove 1710 is disposed on the inner surface of the adjustable ring 1700. FIG. 17C also illustrates holes 1740, which are useful, for example, for securing the adjustable ring 1700 to the graft implant.

Figure 18A:
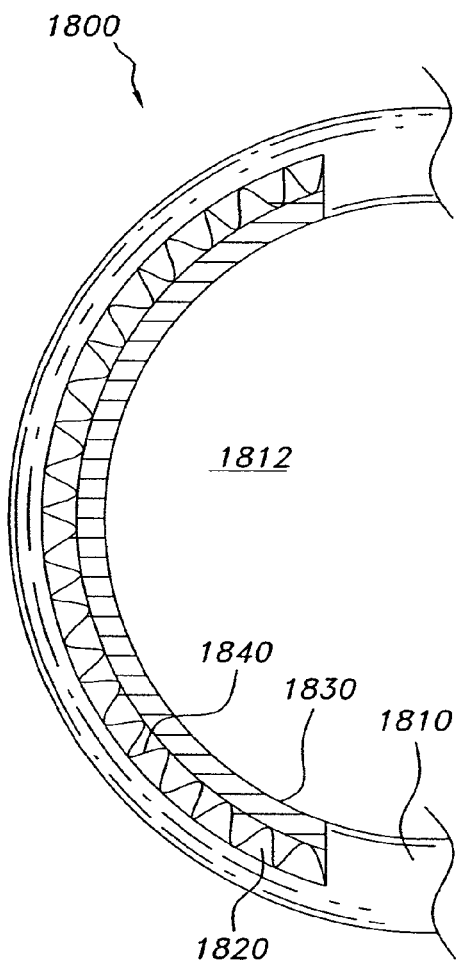
FIG. 18A is a cross-section of an embodiment of an adjustable element in which a shape memory material is disposed in a recess.

FIG. 18A illustrates in cross-section another embodiment of an adjustable element 1800 comprising a body member 1810, which comprises a recess 1820. In the illustrated embodiment, the body member 1810 is generally concave, defining a space 1812. In the illustrated embodiment, the recess 1820 is formed on the concave portion of the body member 1810. A movable member 1830 is disposed in the recess 1820. Between the body member 1810 and the movable member 1830 is disposed a shape memory element 1840. In some embodiments, the body member 1810 is substantially rigid, for example, a metal, a polymer resin, which is reinforced in some embodiments, or a composite. In some embodiments, the movable member 1830 is flexible, elastic, and/or elastomeric, for example, polymers, silicone rubber, synthetic rubber, fabrics, other elastomeric materials known in the art, and combinations and/or composites thereof. In some embodiments, the movable member 1830 is substantially rigid. The shape memory element 1840 comprises one or more suitable shape memory materials disclosed herein, for example, nitinol.

Figure 18B:
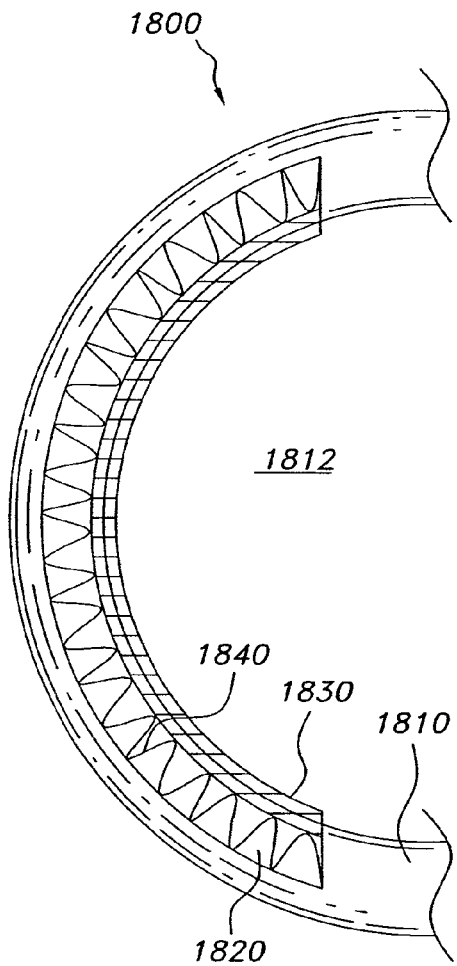
FIG. 18B illustrates the adjustable element of FIG. 18A after adjustment.

FIG. 18B illustrates the adjustable element 1800 after activation. In this case the shape memory element 1840 expands, thereby urging the movable member 1830 into the space 1812, thereby reducing the volume of the space 1812. Those skilled in the art will understand that, in certain embodiments, the adjustable element is configured such that a movable member is disposed on a convex portion of a body member, thereby increasing the diameter of an adjustable element, while in certain embodiments, the adjustable element is configured such that a movable member is disposed on a substantially planar portion of the body member, thereby increasing the length and/or width of the adjustable element.

Figure 19A:
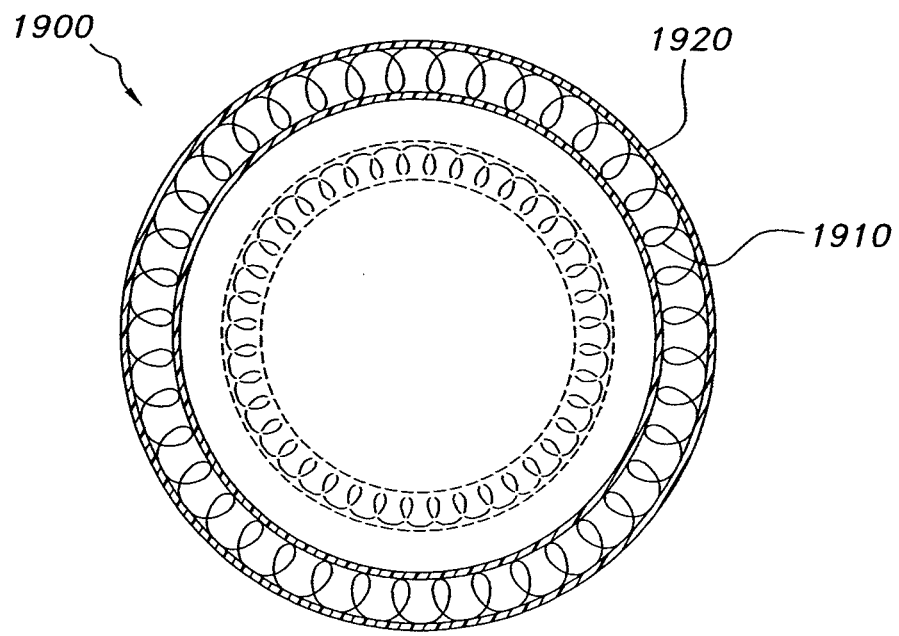
FIGS. 19A and 19B illustrate in cross section two embodiments of adjustable elements with convoluted shape memory elements.
Figure 19B:
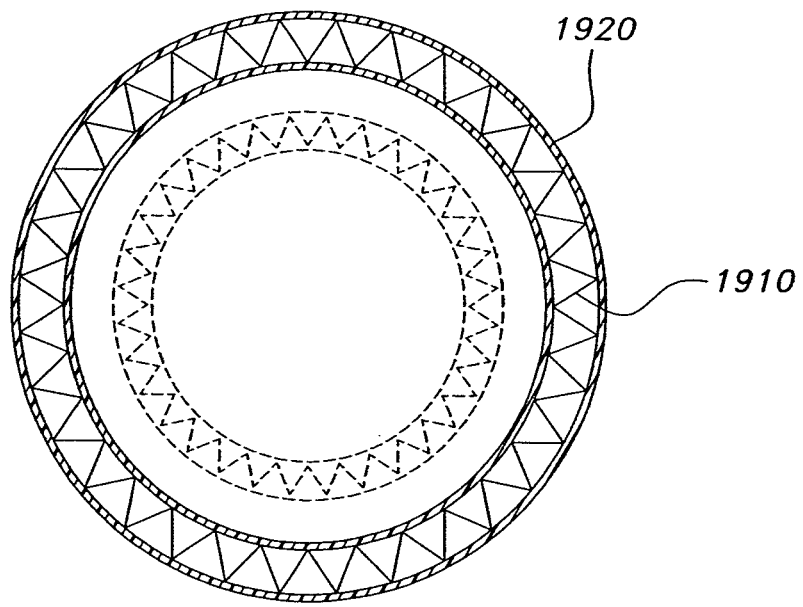

FIGS. 19A and 19B illustrate cross sections of embodiments of adjustable elements 1900 comprising a convoluted shape memory element 1910 and a coating and/or layer 1920 Suitable coatings and/or layer materials are discussed above. In FIG. 19A, the convoluted shape memory element is in the shape of a coil, while in FIG. 19B, it is pleated. The unadjusted sizes of the adjustable elements 1900 are shown in phantom.

Figure 20A:
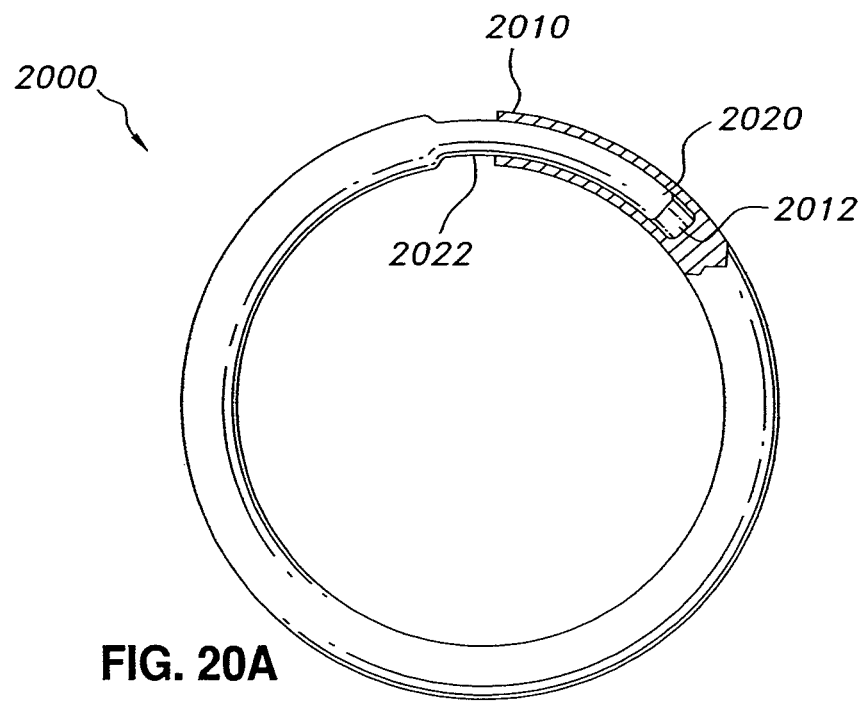
FIG. 20A is a cross-section of an another embodiment of an adjustable element in which a shape memory material is disposed in a recess.
Figure 20B:
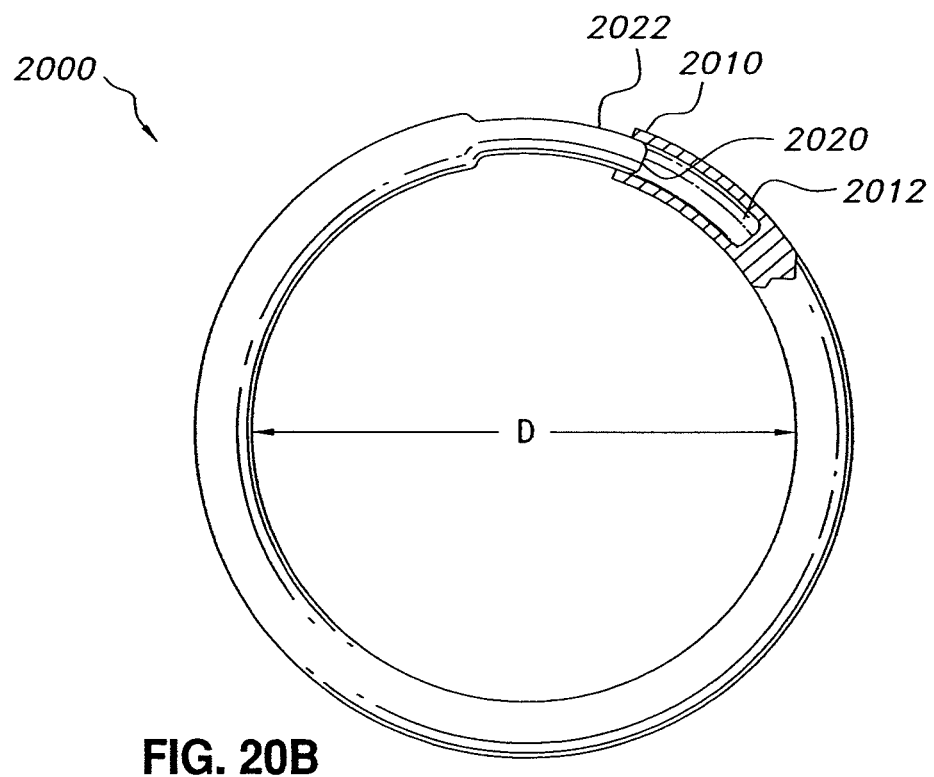
FIG. 20B illustrates the adjustable element of FIG. 20A after adjustment.

FIG. 20A illustrates in partial cross section an embodiment of a generally circular adjustable element 2000 in an unadjusted configuration comprising a first end 2010 and a second end 2020. The first end comprises a recess 2012 into which a reduced diameter portion 2022 of the second end is slidably inserted. FIG. 20B illustrates the adjustable element 2000 of FIG. 20A after adjustment, in which the reduced diameter portion 2022 is partially withdrawn from the recess 2022, and the diameter D of the adjustable element increased.

Figure 21A:
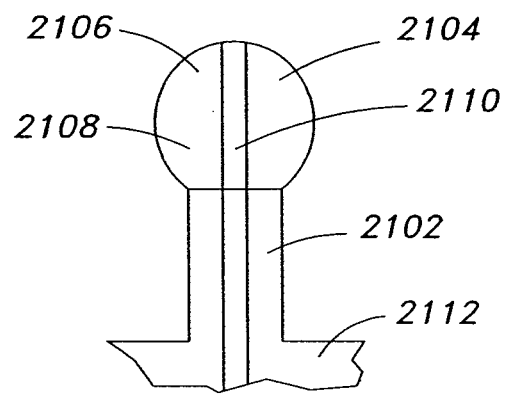
FIG. 21A illustrates an embodiment of an activation post capable of being attached to an adjustable prosthetic valve implant.

FIG. 21A illustrates an embodiment of an activation post 2100 capable of being attached to embodiments of the adjustable prosthetic valve implant as disclosed herein. The activation post 2100, or energy transfer member, is configured to project out into the bloodstream for docking with an catheter configured to adjust an implant.

The activation post 2100 comprises a rod 2102, a sphere 2108, a positive conductive electrode 2104, a negative conductive electrode 2106, and an electrical insulation element 2110. The sphere 2108 is affixed to the end of the rod 2102. In certain embodiments, the electrodes 2104 and 2106 may be operably connected to activation elements in the implant. In certain embodiments, the activation elements can be fabricated from high resistance metals or ceramics such as nickel chromium wire.

Figure 21B:
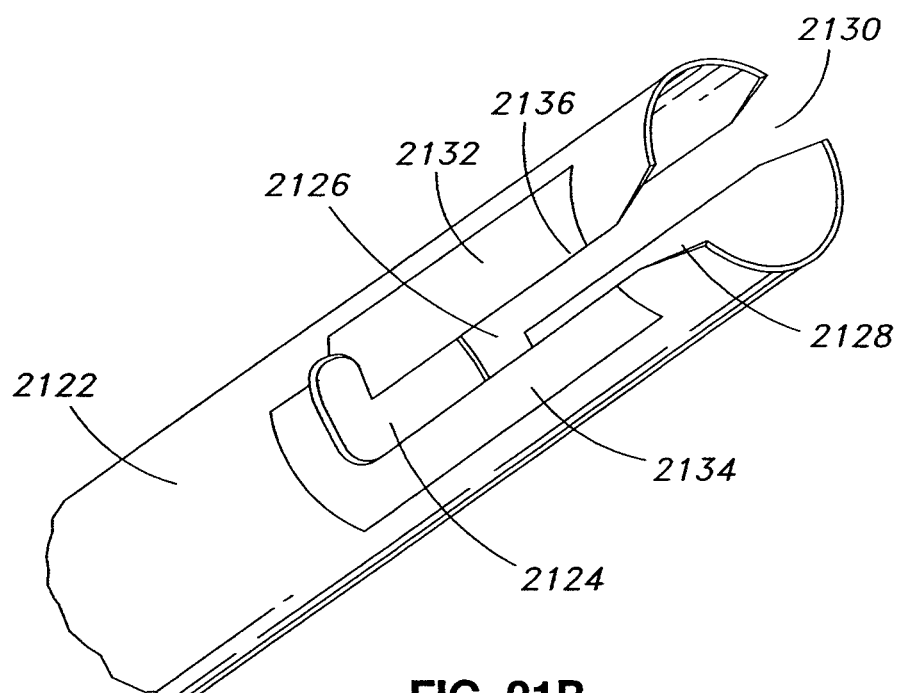
FIG. 21B illustrates a distal end of an embodiment of an adjustment catheter for an adjustable prosthetic valve implant.

FIG. 21B illustrates a distal end of one embodiment of an adjustment catheter 2120 for adjusting embodiments of the adjustable prosthetic valve implant as disclosed herein. The illustrated adjustment catheter 2120 comprises a plurality of keyway slots 2124 and 2126 disposed on opposite sides of the catheter 2120. In certain embodiments, the keyway slots may be located in different positions in relation to one another. Each keyway slot 2124 and 2126 further comprises a plurality of distal lead-in gradual tapers 2130 and 2128. In some embodiments, the inside diameter edges 2136 of the slots 2124 and 2126 or the tapers 2130 and 2128 are sharpened to cut through tissue which can build up around the adjustment post 2100 of FIG. 21A. In certain embodiments, the edges 2136 may also comprise a roughened surface structure in order to abrade away tissue that might interfere with electrical transmission. In certain embodiments, the catheter 2120 further comprises electrodes 2132 and 2134 which are electrically isolated from each other and insulated except at the edges of the slots 2124 and 2126. The electrodes 2132 and 2134 may be operably connected to electrical lines that run the length of the catheter 2120 to the proximal end where they are operably connected to plugs, sockets, or appropriate energy sources. In certain embodiments, an electrode may be connected to an energy source via a lead configured to conduct any form of electromagnetic or mechanical energy, such as a fiber optic wire or electrical wire.

In certain embodiments, when the activation post 2100 comes into contact with an electrode 2132 or 2134, activation energy may be transferred from the catheter 2120 to the The adjustment catheter 2100 may be used to activate an adjustable prosthetic implant as disclosed herein by first connecting an adjustment post 2100 to an interior surface of an implant 2112. In certain embodiments, the opposite end of the adjustment post 2100 may project into the bloodstream. In certain embodiments, the opposite end of the adjustment post 2100 may reside in the same cylindrical region as the implant 2112, where it may contact tissue. In certain embodiments, electrical insulation may be provided to prevent activation energy, such as adjustment currents and voltages, from causing tissue burn. In certain embodiments, guidance of the catheter 2120 to the adjustment post 2120 may be facilitated using external means, such as fluoroscopic guidance or ultrasound imaging. The adjustment post 2100 may be docked with the adjustment catheter 2120 by passing the ball 2108 into the central lumen of the adjustment catheter 2120, then through the tapered opening, 2128 or 2130, and into one of the slots 2124 or 2126. In certain embodiments, the slots 2124 and 2126 may advantageously lock or otherwise securely hold the activation post 2100. Either electrode 2132 or 2134 may thus transfer electrical energy to the implant 2112 through the post 2100. In certain embodiments, alignment of the electrodes 2132 and 2134 with the electrodes 2104 and 2106 facilitates proper electrical energy delivery.

Figure 22:
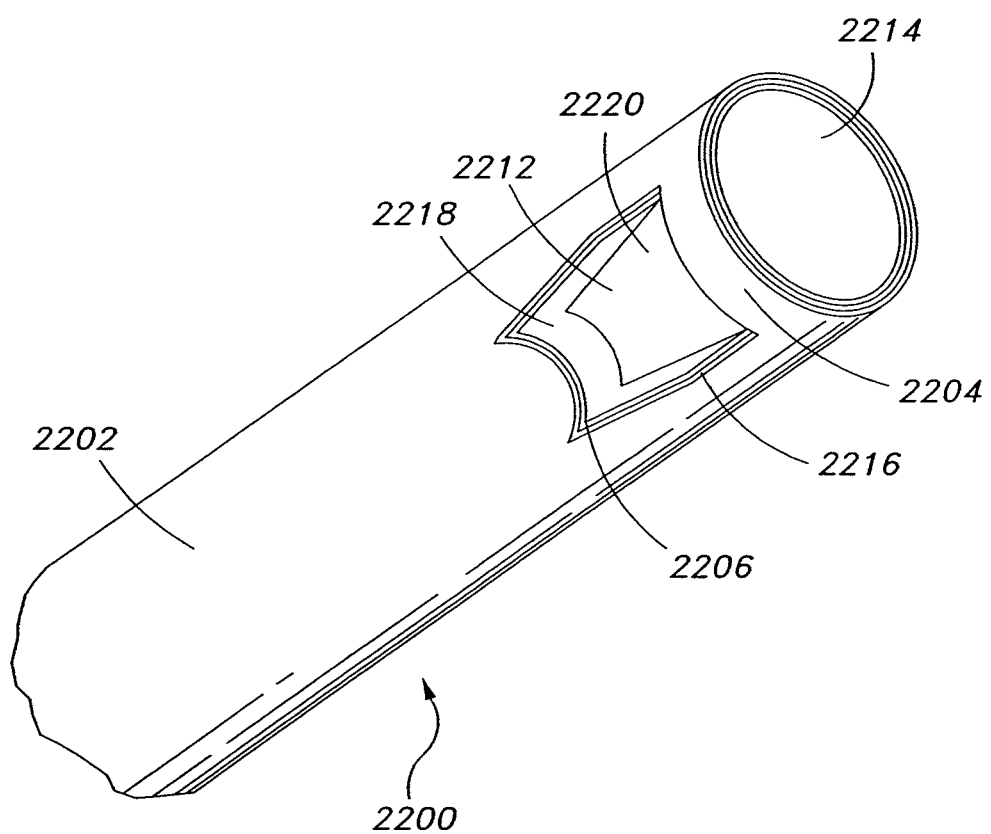
FIG. 22 illustrates a distal end of another embodiment of an adjustment catheter.

FIG. 22 illustrates a distal end of another embodiment of an adjustment catheter 2200 for adjusting embodiments of the adjustable prosthetic valve implant as disclosed herein. The adjustment catheter 2200 comprises an insulating catheter body 2202. The catheter body 2202 comprises a central lumen 2214, a positive electrode 2206 and a negative electrode 2212. In certain embodiments, the negative electrode 2212 is also the outer surface of an inwardly angled tab 2220, which is bent inward and spring loaded to engage the adjustment post 2100 discussed in FIG. 21A. In certain embodiments, the adjustment catheter 2200 may also comprise a cutout 2218. In certain embodiments, the slot edges 2216 can comprise sandpaper-like edges or other roughened surfaces to remove tissue buildup on the post 2100, as described above. In certain embodiments, a plurality of separate and electrically isolated conductors may operably connect the electrodes 2206 and 2212 to the proximal end of the catheter 2200, as described above.

Figure 23A:
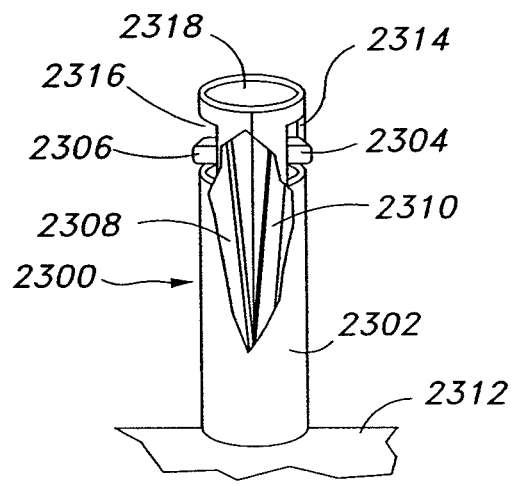
FIG. 23A illustrates an embodiment of an adjustment post connected to a prosthetic valve implant.

FIG. 23A illustrates an adjustment post 2300 connected to a prosthetic valve implant 2312 according to certain embodiments. The adjustment post 2300 comprises a quick release pin 2302, a spring-loaded positive electrode 2304 and a spring-loaded negative electrode 2306. In certain embodiments, the adjustment post 2300 further comprises a central lumen 2318 which may be open or closed at its end. The electrodes 2304 and 2306 may be affixed to spring loaded arms 2310 and 2308 respectively. In certain embodiments, the electrodes 2304 and 2306 may project out through ports 2314 and 2316, respectively, in the post 2302. In certain embodiments, the electrodes 2304 and 2306 may project out in other ways. In certain embodiments, the electrodes 2304 and 2306 may be operably connected to activation elements surrounding the implant 2312. In certain embodiments, the electrodes 2304 and 2306 may be operably connected to activation elements within the implant 2312.

Figure 23B:
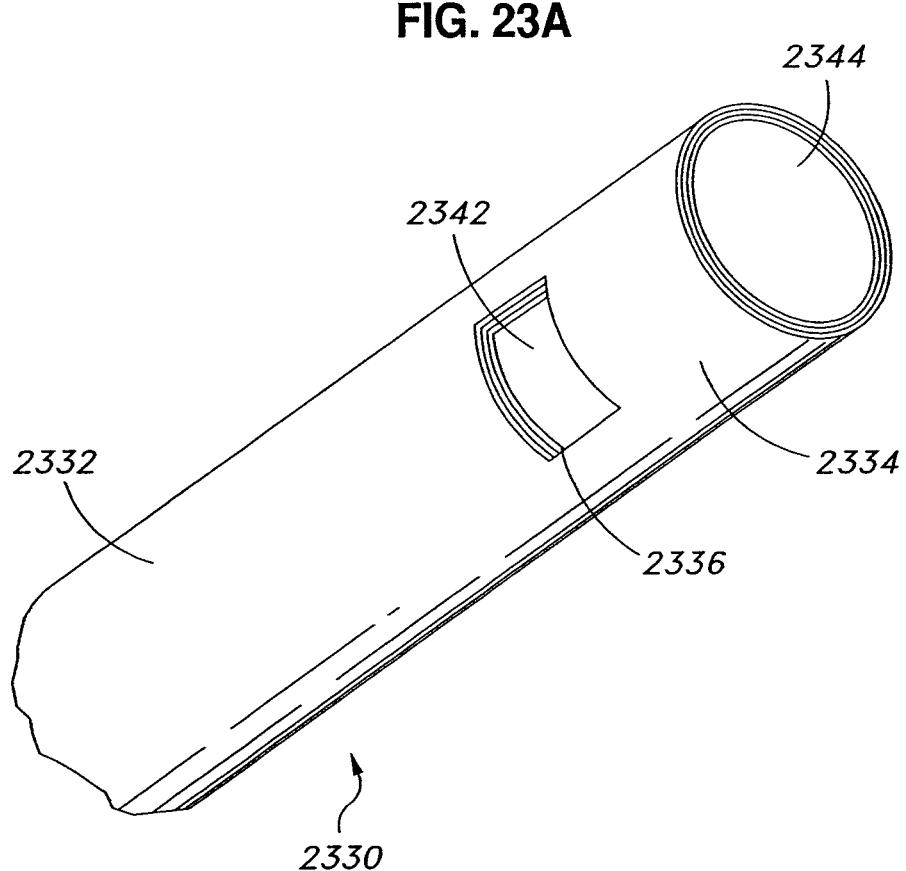
FIG. 23B illustrates a distal end of another embodiment of an adjustment catheter.

FIG. 23B illustrates a distal end of another embodiment of an adjustment catheter 2330 for adjusting embodiments of the adjustable prosthetic valve implant as disclosed herein. The adjustment catheter 2330 comprises a catheter shaft 2332, a central lumen 2344, and a slot 2342. In certain embodiments, the slot 2342 is longer in one direction than another. For example, in the embodiment illustrated, the length of the slot 2342 in the circumferential direction is longer than the length of the slot 2342 in the axial direction. The slot 2342 may provide a communication channel between the central lumen 2344 and the exterior of the catheter 2330. In certain embodiments, the catheter 2330 further comprises at least one positive electrical connector 2336 and at least one negative electrical connector (on the interior wall, not shown). The electrical connectors may be used to engage electrodes 2304 and 2306 on an implant 2312 (FIG. 23A). The electrical connectors on the catheter 2330 may be electrically isolated and operably connected to the proximal end of the catheter 2330, as discussed above.

Figure 24:
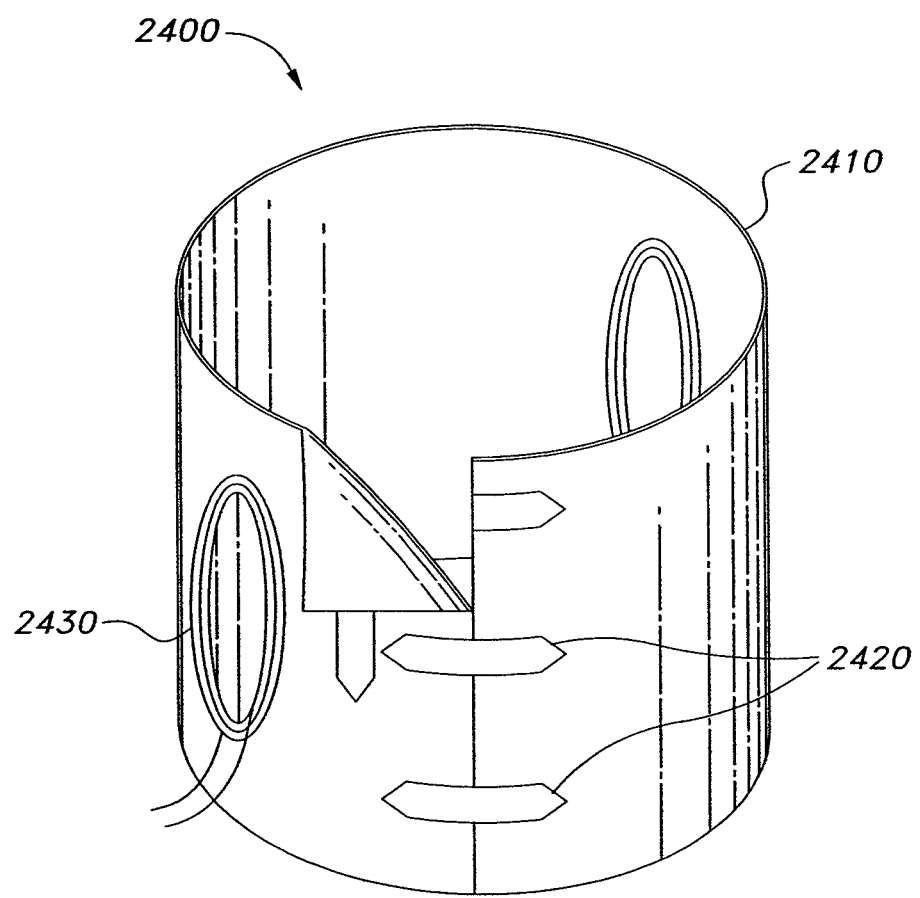
FIG. 24 illustrates an embodiment of a wrappable activation device.

An embodiment of a wrappable inductive activation device 2400 is illustrated in FIG. 24. The device 2400 comprises a wrapping member 2410 dimensioned and configured to wrap around a patient's abdomen. The wrapping member 2400 is at least circumferentially flexible, and comprises a flexible material known in the art, for example, a woven fabric, a non-woven fabric, textile, paper, a membrane and/or film, combinations thereof and the like. In some embodiments, the wrapping member 2410 is at least the circumferentially elastic. In the illustrated embodiment, the wrapping member 2410 comprises a closure 2420, which facilitates securing and removing the device 2400 to and from a patient. Suitable closures 2420 are known in the art, for example, laces, hooks, snaps, buttons, buckles, belts, ties, slide fasteners (Zippers®), hook and loop fasteners (Velcro®), combinations thereof, and the like. The device 1500 also comprises one or more conductive coils 2430, which are used to generate one or more electromagnetic fields for activating the graft implant. Some embodiments comprise circumferential coils.

The electrical current in the coil(s) 2430 is controlled using any suitable controller (not illustrated). In some embodiments, the current control is automated, for example, using a computer, microprocessor, data processing unit, and the like. As discussed above, in some embodiments, the graft implant is dynamically remodeled, that is, the graft implant contemporaneously imaged and adjusted. In some embodiments, the controller is integrated with a system for imaging at least an adjustable element in the graft implant. As discussed above, in some embodiments, an adjustable element is adjusted in steps. Dynamic remodeling permits a user to monitor the effectiveness of each adjustment step.

While certain aspects and embodiments of the invention have been described, these have been presented by way of example only, and are not intended to limit the scope of the invention. Indeed, the novel methods and systems described herein may be embodied in a variety of other forms without departing from the spirit thereof. For example, an implant and adjustment system can be configured to be used in the mitral, pulmonary, or tricuspid position, rather than in the aortic position. The accompanying claims and their equivalents are intended to cover such forms or modifications as would fall within the scope and spirit of the invention.

What is claimed is:

1. A prosthetic implant, for treating a diseased aortic valve, comprising:
   a substantially tubular body configured to be positioned in an aorta of a patient, at or near the patient's aortic valve, the body comprising:
      a lumen extending through the body from a proximal end to a distal end of the body; and
      an adjustable frame surrounding the lumen; and
   at least one adjustable element located in or on the body and extending at least partially around a circumference of the lumen;
   wherein the at least one adjustable element comprises a shape memory material ring and an electrically conductive wire wrapped around the ring, the wire being configured to conduct heat to the ring, so that the at least one adjustable element is transformable, in response to application of an activation energy, from a first configuration to a second configuration, wherein the first configuration and second configuration differ in a size of at least one dimension of the at least one adjustable element; and
   wherein the at least one adjustable element is configured to engage at least one of a root of the aorta, an annulus of the aortic valve, and the patient's left ventricle, when the at least one adjustable element is in the second configuration.

2. The prosthetic implant of claim 1, wherein the at least one adjustable element is coupled to at least one prosthetic aortic valve leaflet.

3. The prosthetic implant of claim 1, wherein the at least one adjustable element comprises a prosthetic aortic valve annulus.

4. The prosthetic implant of claim 1, wherein the shape memory material is selected from the group consisting of shape memory metals, shape memory alloys, shape memory polymers, shape memory ferromagnetic alloys, and combinations thereof.

5. The prosthetic implant of claim 4, wherein the shape memory material comprises nitinol.

6. The prosthetic implant of claim 1, wherein the at least one dimension of the second configuration is greater than the at least one dimension of the first configuration.

7. The prosthetic implant of claim 6, wherein the at least one dimension is a diameter.

8. The prosthetic implant of claim 6, wherein the at least one dimension is a length.

9. The prosthetic implant of claim 1, wherein the at least one dimension of the second configuration is less than the at least one dimension of the first configuration.

10. The prosthetic implant of claim 1, wherein the at least one adjustable element is disposed in proximity to the open end of at least one of the distal end and the proximal end.

11. The prosthetic implant of claim 10, wherein a graft member covers at least a portion of at least one of the at least one adjustable element and the body.

12. The prosthetic implant of claim 10, further comprising at least a second adjustable element disposed between the distal end and the proximal end.

13. The prosthetic implant of claim 1, wherein the frame comprises the at least one adjustable element.

14. The prosthetic implant of claim 1, wherein the frame is expandable.

15. The prosthetic implant of claim 1, wherein the adjustable element comprises a closed ring.

16. The prosthetic implant of claim 15, wherein the closed ring comprises a one-way ratchet.

17. The prosthetic implant of claim 1, wherein the adjustable element comprises an open ring.

18. The prosthetic implant of claim 17, wherein the adjustable element comprises a spiral portion.

19. The prosthetic implant of claim 1, wherein an insulating layer is disposed on at least a portion of the shape memory material.

20. The prosthetic implant of claim 19, wherein portions of the shape memory material are exposed through openings in the insulating layer.

21. The prosthetic implant of claim 1, wherein an energy-absorbing material is disposed on at least a portion of the shape memory material.

22. The prosthetic implant of claim 21, wherein the energy absorbing material absorbs ultrasonic energy.

23. The prosthetic implant of claim 21, wherein the energy absorbing material absorbs radio frequency energy.

24. The prosthetic implant of claim 1, wherein a check valve is affixed to a central region of the body.

25. The prosthetic implant of claim 24, wherein the check valve is a tri-leaflet check valve.

26. The prosthetic implant of claim 1, further comprising an activation post configured to transmit activation energy to the at least one adjustable element.

27. The prosthetic implant of claim 1, further comprising a crown support.

28. A prosthetic implant for treating a diseased valve in a patient's aorta, the prosthetic implant comprising:
   valve means for permitting one-way flow of blood from the patient's left ventricle into the aorta;
   engagement means for engaging at least one of a root of the aorta, an annulus of the aortic valve, and the patient's left ventricle, the engagement means being coupled to the valve means;
   support means for supporting the valve means and coupled to the valve means, the support means being configured to extend distally into the ascending aorta beyond the aortic valve annulus when the valve means is in position at the aortic valve;
   wherein a wire is wrapped around the engagement means, the wire being configured to conduct heat to the engagement means, so that the engagement means is adjustable from a first configuration to a second configuration in response to an activation energy established using an energy source external to the patient's body, wherein the first configuration and second configuration differ in size in at least one dimension; and
   wherein the engagement means engages the at least one of the root of the aorta, the annulus of the aortic valve, and the patient's left ventricle, when in the second configuration.

* * * * *